United States Patent
Gilbo et al.

(10) Patent No.: US 11,644,520 B2
(45) Date of Patent: May 9, 2023

(54) SYSTEMS AND METHODS FOR MAGNETIC RESONANCE BASED SKULL THERMOMETRY

(71) Applicant: University of Virginia Patent Foundation, Charlottesville, VA (US)

(72) Inventors: Yekaterina K. Gilbo, Charlottesville, VA (US); Helen L. Sporkin, Charlottesville, VA (US); Samuel W. Fielden, Lewisburg, PA (US); John P. Mugler, III, Charlottesville, VA (US); Grady W. Miller, IV, Charlottesville, VA (US); Steven P. Allen, Charlottesville, VA (US); Craig H. Meyer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 177 days.

(21) Appl. No.: 17/144,319

(22) Filed: Jan. 8, 2021

(65) Prior Publication Data
US 2021/0208225 A1    Jul. 8, 2021

Related U.S. Application Data

(60) Provisional application No. 62/958,478, filed on Jan. 8, 2020.

(51) Int. Cl.
*G01R 33/48* (2006.01)
*G01R 33/561* (2006.01)
(Continued)

(52) U.S. Cl.
CPC ..... *G01R 33/4814* (2013.01); *G01R 33/3804* (2013.01); *G01R 33/4816* (2013.01);
(Continued)

(58) Field of Classification Search
CPC ............ G01R 33/3804; G01R 33/4814; G01R 33/4816; G01R 33/4818; G01R 33/50; G01R 33/561
See application file for complete search history.

(56) References Cited

U.S. PATENT DOCUMENTS

| 7,583,082 B1 | 9/2009 | Hu et al. |
| 7,642,777 B1 | 10/2010 | Meyer et al. |

(Continued)

FOREIGN PATENT DOCUMENTS

| WO | 2010/062557 | 6/2010 |
| WO | 2012/145547 | 10/2012 |

(Continued)

OTHER PUBLICATIONS

G. Pinton, J. Aubry, E. Bossy, M. Muller, and M. Pernot, "Attenuation, scattering, and absorption of ultrasound in the skull bone."

(Continued)

*Primary Examiner* — Gregory H Curran
(74) *Attorney, Agent, or Firm* — Meunier Carlin & Curfman LLC

(57) ABSTRACT

Described herein are systems, methods, and computer-readable medium for magnetic resonance (MR) based thermometry. In one aspect, in accordance with one embodiment, a method for magnetic resonance based thermometry includes: acquiring, by a variable flip-angle T1 mapping sequence, MR data in an area of interest of a subject that is heated by the application of focused ultrasound (FUS) to the brain of the subject, where the MR data includes T1 values over time, and where the acquisition of the MR data includes applying an accelerated three-dimensional ultra-short spiral acquisition sequence with a nonselective excitation pulse; and determining, based at least in part on a mathematical relationship established by T1 mapping thermometry, a temperature change in the area of interest over time, and (Continued)

where the temperature change is caused at least in part by a change in the applied FUS.

27 Claims, 34 Drawing Sheets
(25 of 34 Drawing Sheet(s) Filed in Color)

(51) Int. Cl.
    *G01R 33/38*     (2006.01)
    *G01R 33/50*     (2006.01)

(52) U.S. Cl.
    CPC ......... *G01R 33/4818* (2013.01); *G01R 33/50* (2013.01); *G01R 33/561* (2013.01)

(56) References Cited

U.S. PATENT DOCUMENTS

| | | | |
|---|---|---|---|
| 7,813,537 B2 | 10/2010 | Epstein et al. | |
| 7,888,935 B1 | 2/2011 | Tan et al. | |
| 8,026,720 B1 | 9/2011 | Chen et al. | |
| 8,094,907 B1 | 1/2012 | Meyer et al. | |
| 8,238,634 B1 | 8/2012 | Meyer et al. | |
| 8,306,289 B1 | 11/2012 | Meyer et al. | |
| 8,440,167 B2 | 5/2013 | Beller et al. | |
| 8,700,127 B2 | 4/2014 | Salerno et al. | |
| 9,183,626 B2 | 11/2015 | Zhao et al. | |
| 9,224,210 B2 | 12/2015 | Epstein et al. | |
| 9,322,896 B2 | 4/2016 | Fielden et al. | |
| 9,589,345 B2 | 3/2017 | Zhao et al. | |
| 9,651,645 B2 | 5/2017 | Fielden et al. | |
| 9,811,924 B2 | 11/2017 | Johnson et al. | |
| 9,874,623 B2 | 1/2018 | Fielden et al. | |
| 9,910,118 B2 | 3/2018 | Feng et al. | |
| 9,953,439 B2 | 4/2018 | Salerno et al. | |
| 9,989,611 B2 | 6/2018 | Zhao et al. | |
| 10,143,384 B2 | 12/2018 | Chen et al. | |
| 10,310,047 B2 | 6/2019 | Cai et al. | |
| 10,314,511 B2 | 6/2019 | Meyer et al. | |
| 2008/0161784 A1* | 7/2008 | Hogan | G01R 33/4814 600/410 |
| 2010/0116810 A1 | 5/2010 | Faries, Jr. et al. | |
| 2014/0044335 A1 | 2/2014 | Johnson et al. | |
| 2015/0282719 A1 | 10/2015 | Fielden et al. | |
| 2015/0282733 A1* | 10/2015 | Fielden | A61B 5/055 600/411 |
| 2015/0287222 A1 | 10/2015 | Zhao et al. | |
| 2017/0035301 A1* | 2/2017 | Lechner-Greite | A61B 5/7285 |
| 2017/0035319 A1 | 2/2017 | Zhao et al. | |
| 2017/0202478 A1 | 7/2017 | Handsfield et al. | |
| 2017/0307705 A1 | 10/2017 | Mugler et al. | |
| 2017/0328972 A1 | 11/2017 | Fielden et al. | |
| 2018/0292499 A1 | 10/2018 | Meyer et al. | |
| 2019/0279361 A1 | 3/2019 | Meyer et al. | |
| 2019/0302210 A1 | 10/2019 | Epstein et al. | |
| 2019/0302211 A1 | 10/2019 | Cai et al. | |

FOREIGN PATENT DOCUMENTS

| | | |
|---|---|---|
| WO | 2013/023214 | 2/2013 |
| WO | 2016/004423 | 1/2016 |

OTHER PUBLICATIONS

M. L. Schwartz et al., "Skull bone marrow injury caused by MR-guided focused," J. Neurosurg., vol. 130, No. March, pp. 1-5, 2018.

M. Han et al., "Quantifying temperature-dependent T1 changes in cortical bone using ultrashort echo-time MRI," Magn. Reson. Med., vol. 74, No. 6, pp. 1548-1555, 2015.

Deoni, S. C., Rutt, B. K. and Peters, T. M. (2003), Rapid combined T1 and T2 mapping using gradient recalled acquisition in the steady state. Magn. Reson. Med., 49: 515-526. doi:10.1002/mrm.10407.

M. Fielden, Mugler, Miller, Pauly, "Abstract: Detecting Signal Changes in Heated Bone w/3D Spiral Ultra-Short Echo Time Sequence," p. 3867, 2014.

Odeen, Henrik, and Dennis L. Parker. "Non-Invasive Thermometry with Magnetic Resonance Imaging." Theory and Applications of Heat Transfer in Humans, 2018, pp. 267-299., doi:10.1002i9781119127420.ch15.

Odeen Henrik, Bolster B., Jeong E. Parker D. "Investigation of temperature dependent changes in signal intensity, T1 and T2* in cortical bone". Abstract In: ISMRM 2016.

Miller, "MR bone imaging," J. Ther. Ultrasound, vol. 3, No. Suppl 1, p. O37, 2015.

Ramsay, Elizabeth, et al. "Temperature-Dependent MR Signals in Cortical Bone: Potential for Monitoring Temperature Changes during High-Intensity Focused Ultrasound Treatment in Bone." Magnetic Res Med, vol. 74, No. 4, 2014, pp. 1095-1102. doi:10.1002/mrm.25492.

* cited by examiner

100

---

ACQUIRE, BY A VARIABLE FLIP-ANGLE (VFA) T1 MAPPING SEQUENCE, MR DATA CORRESPONDING TO CORTICAL BONE OF AT LEAST PART OF THE SKULL OF A SUBJECT THAT IS HEATED BY THE APPLICATION OF FOCUSED ULTRASOUND (FUS), APPLYING AN ACCELERATED THREE-DIMENSIONAL (3D) ULTRA-SHORT (UTE) SPIRAL ACQUISITION SEQUENCE WITH A NONSELECTIVE EXCITATION PULSE. — 102

BASED ON A MATHEMATICAL RELATIONSHIP ESTABLISHED BY T1 MAPPING THERMOMETRY, DETERMINE A TEMPERATURE CHANGE IN THE CORTICAL BONE. — 104

*FIG. 1*

| Echo Time | Temporal Resolution | Spatial Resolution | FOV (3D) |
|---|---|---|---|
| ≤ 100µs | ≤ 90s | ≤ 5 x 5 x 5 mm | ≥ 280 x 280 x 200 mm |

*FIG. 2*

FIG. 22A
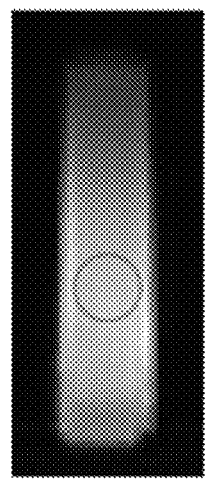
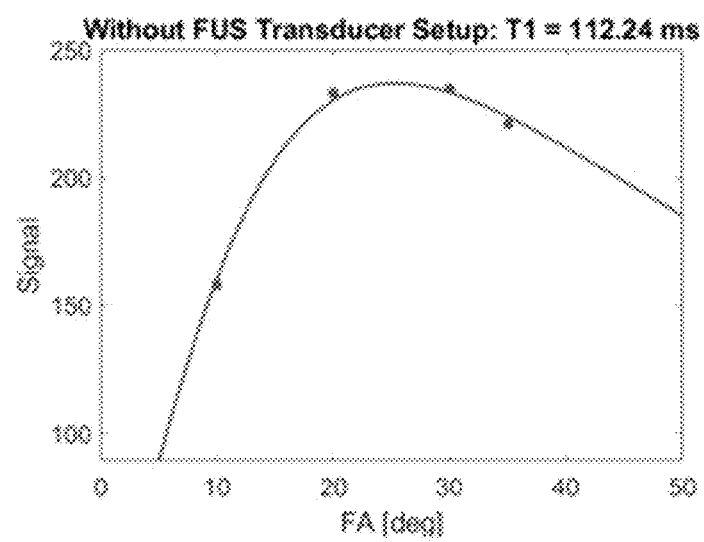
FIG. 22B
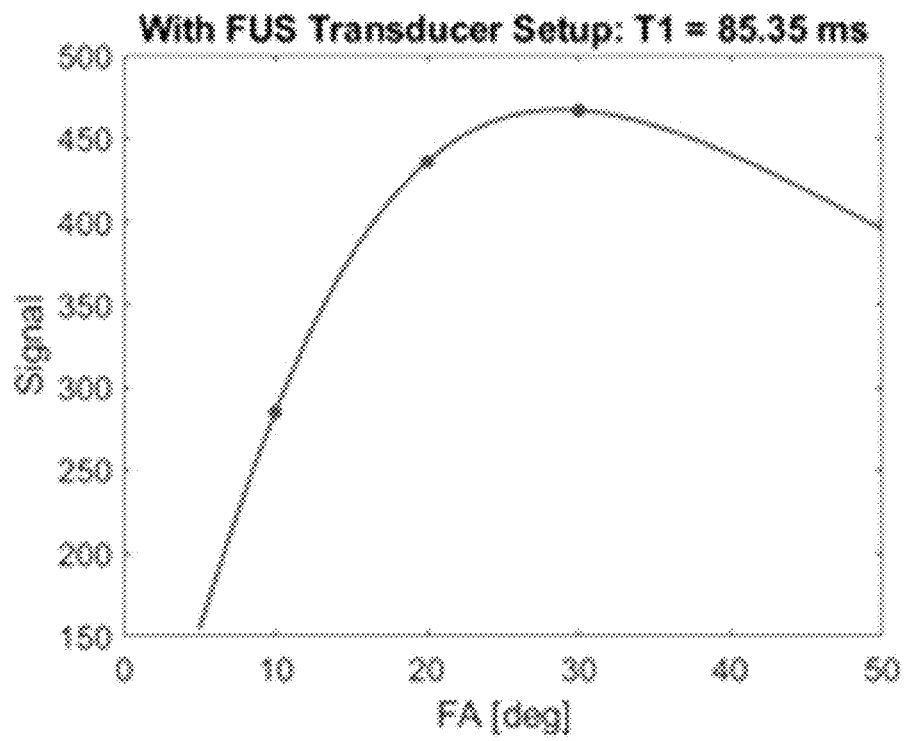

_SYSTEMS AND METHODS FOR MAGNETIC RESONANCE BASED SKULL THERMOMETRY_

CROSS-REFERENCE TO RELATED APPLICATIONS

This application claims priority to and the benefit of U.S. provisional patent application No. 62/958,478, filed on Jan. 8, 2020, and titled "System and Method for T1-based Skull Thermometry using a 3D Spiral Ultra-Short Echo Time Sequence," the disclosure of which is hereby incorporated by reference herein in its entirety.

STATEMENT OF GOVERNMENT RIGHTS

This invention was made with government support under grant numbers EB022309 and EB028773 awarded by the National Institutes of Health. The government has certain rights in the invention.

BACKGROUND

Magnetic resonance guided focused ultrasound (MRgFUS) can enable brain surgery with focused ultrasound (FUS) waves mechanically perturbing or heating brain tissue. The procedure can be performed by placing a patient's head into a FUS helmet composed of a number of transducers (e.g. 1024 transducers). By computing the timing at which transducers need to turn on (phase delays) to focus the waves at a specific spot, a surgeon can destroy the targeted tissue to millimeter precision at ablative temperatures (55-60° C.) with no damage to surrounding tissue and thereby treat different disorders. An MRI is used to image the target and to determine the coordinates for the FUS system as well as to monitor the effect of the treatment through changes in T1, T2, and diffusion of the target. For example, MRgFUS has been successfully applied to treat patients with essential tremor (ET). Patients with ET have a tremor typically affecting their hands and quality of life making functional activities such as drinking a glass of water, dressing, or writing very difficult. Ablation of the thalamus in the brain helps to suppress the tremor observed during and immediately after the procedure. MRgFUS in the brain can also treat the symptoms of Parkinson's disease, neuropathic pain, and brain tumors. Though MRgFUS is a rapidly growing technology in interventional radiology and functional neurosurgery, there remain many technical challenges to be solved so that MRgFUS can be a widespread treatment option for neuropathology.

Examples of medical applications include FDA approved treatment for Parkinson's disease and essential tremor and many other disorders in the research stage such as neuropathic pain, depression, and obsessive-compulsive disorder. One challenge to treatment efficacy is posed by the skull. Its high absorption of ultrasound waves creates difficulties, one of which is skull heating. Damage from skull heating has been observed in several patients. Though damage has not been shown to be harmful, it may be linked to problems such as headaches during treatment. Temperature monitoring of the skull would increase treatment safety, enable further development of MRgFUS therapy to non-central brain targets, and potentially speed up treatment by decreasing waiting time between sonications for patients. MRI based thermometry is well suited for this task as monitoring of the brain temperature is already done by MRI.

Bone can attenuate ultrasound energy 20 times more efficiently than soft tissue. Heating of the skull during FUS therapy can be a major concern and limit the amount of acoustic energy that can be safely transmitted into the brain and constrain which parts of the brain can be targeted. Targets away from the center of the brain lead to more skull heating. Despite current clinical precautions such as cooling the scalp actively with circulating water, there is still potential for injury. A recent study has shown that MRgFUS led to unintended skull lesions in 16 out of 40 MRgFUS procedures. Real-time skull thermometry can validate proposed skull heating models and prevent unintended injury to patients. It can also make treatment faster as surgeons can wait 6-15 minutes for the skull to cool in between sonications during the long (e.g. three hour) treatment in which the patient is awake in the MRI and their skull is pinned to a frame. If the skull is shown to have returned to thermal baseline, the treatment can continue more quickly. Lastly, monitoring of skull heating would enable the development of MRgFUS for less central targets, such as for treatment of depression.

It is with respect to these and other considerations that the various aspects of the present disclosure as described below are presented.

SUMMARY

In some aspects, the present disclosure relates to systems, methods, and computer-readable medium for magnetic resonance (MR) based thermometry. In one aspect, the present disclosure relates to a method which, in one embodiment includes acquiring, by a variable flip-angle (VFA) T1 mapping sequence, MR data in an area of interest of a subject corresponding to cortical bone of at least part of the skull that is heated by the application of focused ultrasound (FUS) to a selective portion of the brain of the subject, where the MR data includes a plurality of T1 values over time that include a first point in time and a second, later point time, and where the acquisition of the MR data includes applying an accelerated three-dimensional (3D) ultra-short (UTE) spiral acquisition sequence with a nonselective excitation pulse. The method also includes determining, based at least in part on a mathematical relationship established by T1 mapping thermometry produced according to the T1 mapping sequence, a temperature change in the cortical bone that occurs between the first point in time and the second point in time, and where the temperature change is caused at least in part by a change in the applied FUS.

In another aspect, the present disclosure relates to a system for magnetic resonance (MR) based thermometry, which in one embodiment includes a magnetic resonance imaging (MRI) device configured to acquire, by implementing a variable flip-angle (VFA) T1 mapping sequence, MR data in an area of interest of a subject corresponding to cortical bone of at least part of the skull that is heated by the application of focused ultrasound (FUS) to a selective portion of the brain of the subject, where the MR data includes a plurality of T1 values over time that include a first point in time and a second, later point time, and where the MRI device is further configured to acquire the MR data using an accelerated three-dimensional (3D) ultra-short (UTE) spiral acquisition sequence with a nonselective excitation pulse. The system also includes a processor coupled to the MRI device and configured to cause the system to perform functions that include determining, based at least in part on a mathematical relationship established by T1 mapping thermometry produced according to the T1 mapping sequence, a temperature change in the cortical bone that occurs between the first point in time and the second point in time, and where the temperature change is caused at least in part by a change in the applied FUS.

In another aspect, the present disclosure relates to a non-transitory computer-readable medium having stored instructions that, when executed by one or more processors of a computing device, cause a system for magnetic resonance (MR) based thermometry to perform specific functions. In one embodiment, the specific functions performed include: acquiring, by a variable flip-angle (VFA) T1 mapping sequence, MR data in an area of interest of a subject corresponding to cortical bone of at least part of the skull that is heated by the application of focused ultrasound (FUS) to a selective portion of the brain of the subject, where the MR data includes a plurality of T1 values over time that include a first point in time and a second, later point time, and where the acquisition of the MR data includes applying an accelerated three-dimensional (3D) ultra-short (UTE) spiral acquisition sequence with a nonselective excitation pulse; and determining, based at least in part on a mathematical relationship established by T1 mapping thermometry produced according to the T1 mapping sequence, a temperature change in the cortical bone that occurs between the first point in time and the second point in time, and where the temperature change is caused at least in part by a change in the applied FUS.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with color drawing(s) will be provided by the Office upon request and payment of the necessary fee.

FIG. 1 is a flow diagram showing operations of a method for performing accelerated T1 thermometry in accordance with an embodiment of the present disclosure.

FIG. 2 is a table illustrating non-limiting examples of clinical parameters that can be achieved using embodiments of the present disclosure.

FIGS. 4A-4B are illustrations of UTE VIBE data, wherein FIG. 4A is an illustration of simulated data showing the relationship between the duration of the UTE VIBE vs kz number wherein. zRes=5 mm, zFOV=30 cm; and FIG. 4B is an illustration of Echo Time vs. kz. zRes=5 mm, zFOV=30 cm FIGS. 5A-5B illustrate simulated MR data showing how kz dependent T2 decay leads to blur in Z with zRes=5 mm, and zFOV=30 cm, wherein FIG. 5A illustrates the relationship between T2 decay and kz; and FIG. 5B illustrates the relationship between the signal and Z.

FIGS. 10A-10C illustrate the accuracy of T1 thermometry, wherein FIG. 10A illustrates the accuracy of the T1-Mapping Method using IR, FIG. 10B illustrates the bone thermometry method using VFA, and FIG. 10C illustrates a comparison of the accuracy of T1 derived from VFA to T1 from IR and compares the methods to the expected result.

FIGS. 11A-11B illustrate an experimental setup and result for a water bath cooling experiment, wherein FIG. 11A illustrates the location of two thermocouples in a sample, and FIG. 11B illustrates the experimental result.

FIGS. 12A-12B illustrate an experimental setup and result for a water bath heating experiment, wherein FIG. 12A illustrates the experimental configuration; and FIG. 12B illustrates the experimental result.

FIGS. 13A-13B illustrate the relationships between different T1 signals and temperature in bone for various experiments, wherein FIG. 13A illustrates the relationship between changes in T1-weighted signal vs. temperature in bone, and FIG. 13B illustrates the relationship between a change in T1 vs. temperature in Bone. In FIG. 13A it can be seen that T1-weighted signal vs. temperature is inconsistent in its dependence on temperature, whereas in FIG. 13B, the same bone sample and ROI, the T1 absolute value is consistently linear with temperature ($m_{ave}$=0.98+/−0.15 ms/° C.).

FIG. 14A illustrates the measured T1-weighting sensitivity for different flip angles. FIG. 14B illustrates T1-weighted Signal vs. Temperature in Cow Bone, where the signal behavior with temperature is nonlinear, even at higher flip angles (43.5°).

FIGS. 15A-15B illustrate an experimental result corresponding to a location on a particular bone, wherein FIG. 15A illustrates the location the data was sampled from, and FIG. 15B illustrates the relationship between the T1 signal and temperature.

FIGS. 16A-16B illustrate simulated signal vs. temperature with T1 and T2 weighting, wherein FIG. 16A illustrates a simulation with the parameters T1 (25 C)=120 ms, T1/Temp=1.2 ms/C, TE=0 ms, TR=11 ms; and FIG. 16B illustrates a simulation with the parameters T2 (25 C)=0.2 ms, T2/Temp=4 ms/C, TE=80 us.

FIGS. 17A-17B illustrate an sVFA acceleration experiment wherein FIG. 17A illustrates an experimental configuration; FIG. 17B illustrates the relationship between bone T1 and temperature, FIG. 17B illustrates how the sVFA results show a smaller slope and can underestimate the T1 and FIG. 17C illustrates how for $NiCl_2$ nominal VFA shows good linearity and slope. sVFA without correction can overestimate T1 especially at higher Temperatures. sVFA with correction decreases overestimation but not completely.

FIGS. 18A-18B illustrate T1 vs. temperature for an ex-vivo human skull, wherein FIG. 18A illustrates how under sampling can decrease the signal amplitude and slightly underestimate T1; and FIG. 18B illustrates how the results can be ROI-dependent, but T1 vs. temperature can show a consistently positive slope of varying magnitude.

FIG. 20A illustrates the experimental configuration, FIG. 20B illustrates the linear change in T1 and temperature, and FIG. 20C illustrates the T1 difference map. The T1 difference map shows heating occurred at the bottom of the bone. The data was temporally averaged with a time window of 2 as a less optimal coil was used in this experiment than in other water bath experiments described herein.

FIGS. 22A-22D illustrate results before and after the RF Flip Angle Calibration, wherein FIG. 22A illustrates results before RF Flip Angle Calibration without the FUS transducer setup;

FIG. 22B illustrates results before RF Flip Angle Calibration without the FUS transducer setup;

FIG. 22C represents a plot of signal vs. voltage after RF Flip Angle Calibration; and FIG. 22D illustrates the results with the FUS transducer setup after RF Flip Angle Calibration.

DETAILED DESCRIPTION

Figure 3:
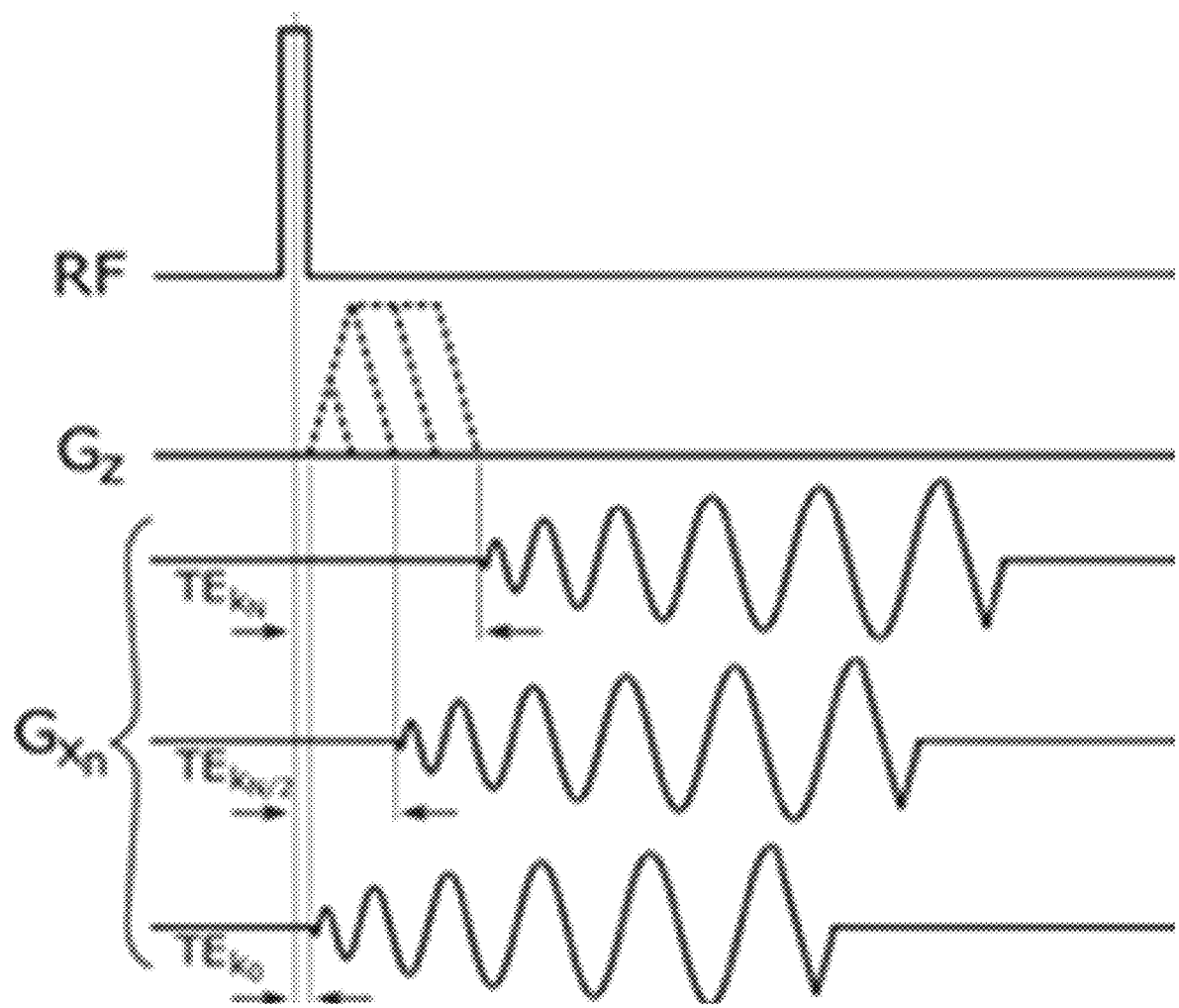
FIG. 3 is an illustration of the UTE VIBE sequence for magnetic resonance data acquisition.
Figure 4A:
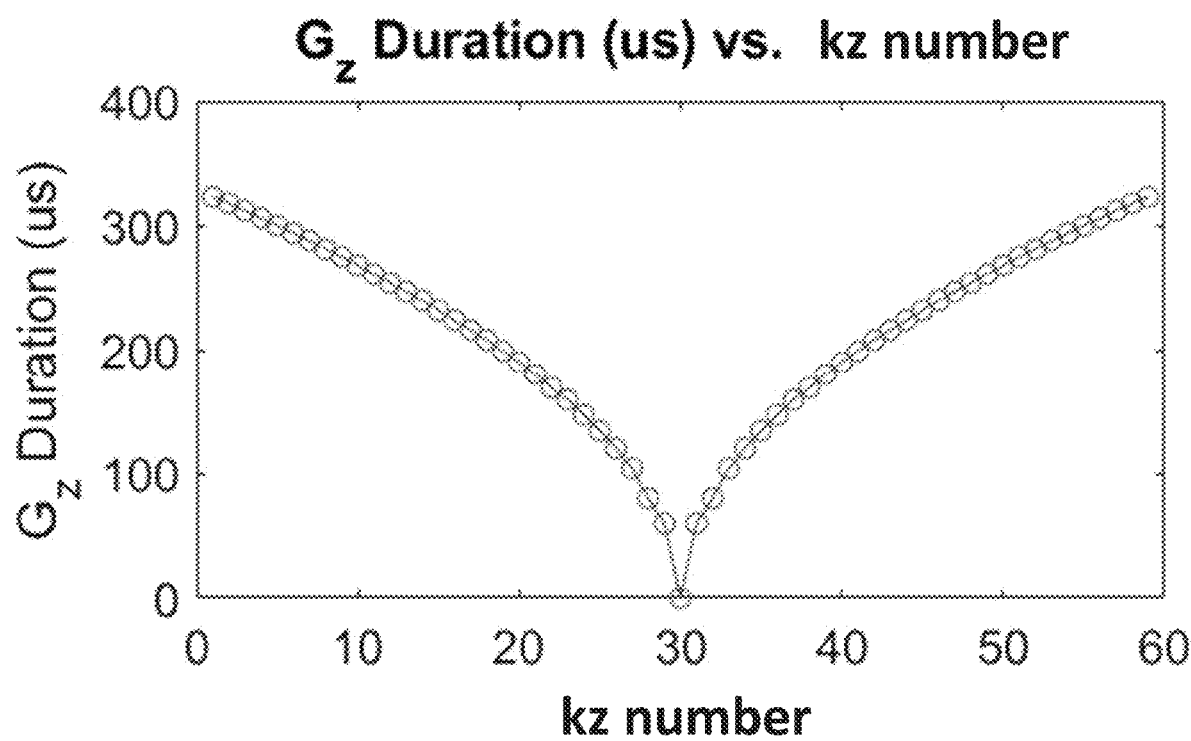
Figure 4B:
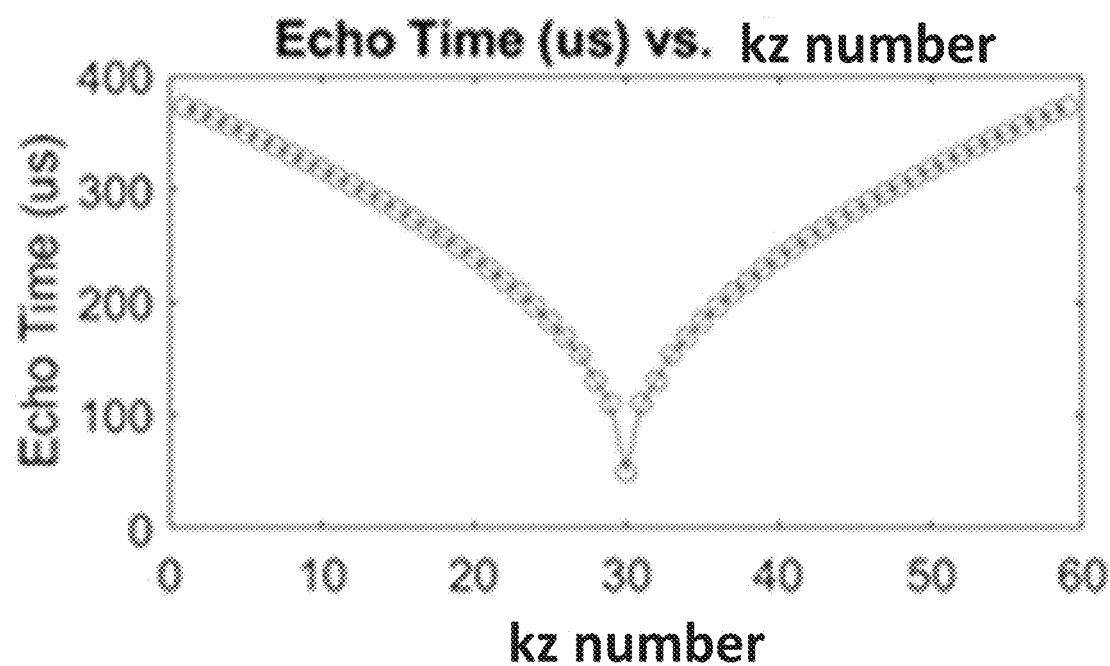

In some aspects, the disclosed technology relates to systems, methods, and computer-readable medium for magnetic resonance based skull thermometry. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

A detailed description of aspects of the disclosed technology, in accordance with various example embodiments, will now be provided with reference to the accompanying drawings. The drawings form a part hereof and show, by way of illustration, specific embodiments and examples. In referring to the drawings, like numerals represent like elements throughout the several figures.

Embodiments of the present disclosure include MRI-based thermometry techniques. In some embodiments of the present disclosure, the MRI-based thermometry technique is adapted to measure heating in the skull of a human patient during a focused ultrasound (FUS) treatment.

Figure 23:
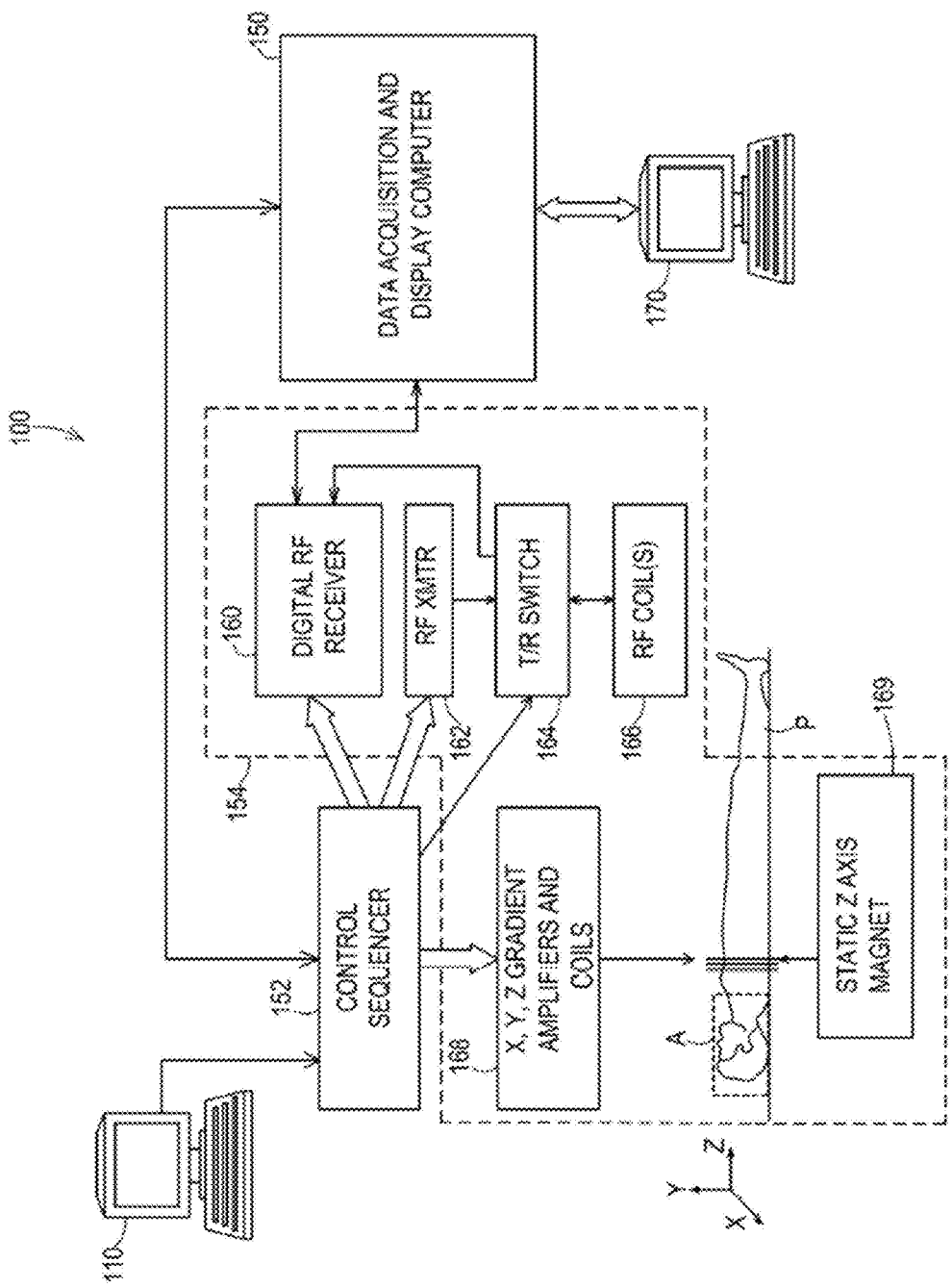
FIG. 23 is a system diagram illustrating an imaging system capable of implementing aspects of the present disclosure in accordance with one or more embodiments.

FIG. 23 is a system diagram illustrating an imaging system capable of implementing aspects of the present disclosure in accordance with one or more example embodiments. FIG. 23 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example to implement magnetic resonance imaging sequences in accordance with various embodiments of the present disclosure. Reconstructed images, such as contrast-enhanced image(s) of an area of interest A of the subject P may be shown on display 170.

The area of interest A shown in the example embodiment of FIG. 23 corresponds to a head region of subject P, but it should be appreciated that the area of interest for purposes of implementing various aspects of the disclosure presented herein is not limited to the head area. It should be recognized and appreciated that the area of interest in various embodiments may encompass various areas of subject P associated with various physiological characteristics, such as, but not limited to the head and brain region, chest region, heart region, abdomen, upper or lower extremities, or other organs or tissues. Various aspects of the present disclosure are described herein as being implemented on portions of the skeletal system of human subjects, for example cortical bone tissue.

It should be appreciated that any number and type of computer-based medical imaging systems or components, including various types of commercially available medical imaging systems and components, may be used to practice certain aspects of the present disclosure. Systems as described herein with respect to imaging are not intended to be specifically limited to the particular system shown in FIG. 23. Likewise, systems as described herein with respect to the application of localized energy for heating certain areas for thermal treatment are not intended to be specifically limited to the particular systems shown in FIG. 24 or described below.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 24:
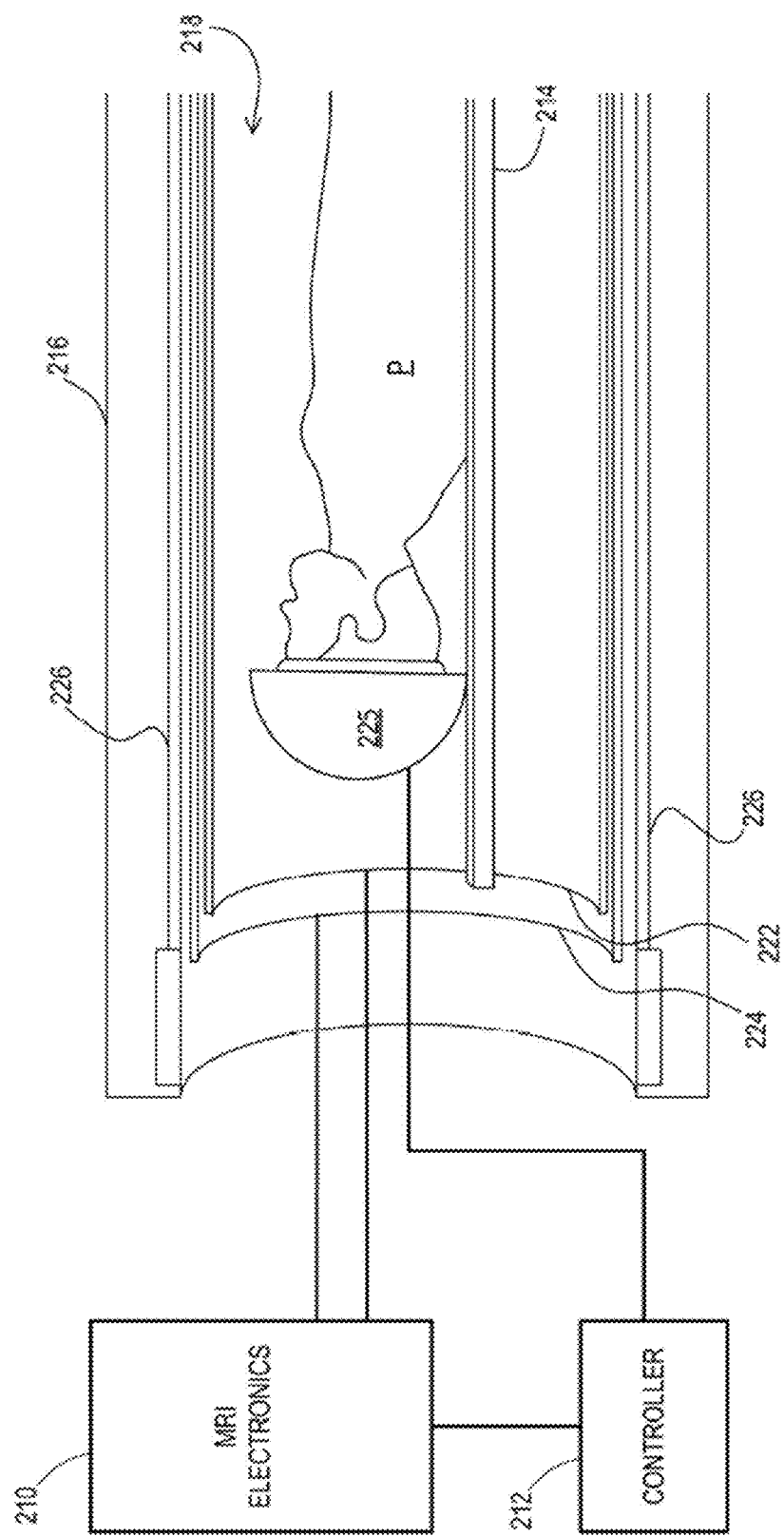
FIG. 24 is a diagram showing an example embodiment of a system with thermal therapy used with MRI, which is capable of implementing aspects of the present disclosure in accordance with one or more embodiments.

FIG. 24 is a diagram showing an embodiment of a system with focused ultrasound (FUS) used with MRI, each of which is capable of implementing aspects of the present disclosure in accordance with one or more embodiments. The MRI system may comprise one or more components of the system 100 shown in FIG. 23. As shown, RF coils 222, gradient coils 224, static Z axis magnet 226, and magnetic housing 216 surround the patient P when the patient is positioned on the table 214 inside of the MRI bore 218. A controller 212 communicates with MRI system electronics 210 as well as the FUS device (225). The MRI system electronics 210 can include one or more components of the MRI subsystem 154 shown in FIG. 23. A user computer (not shown) may communicate with the controller 212 for control of the MRI system and FUS device functions.

In FIG. 24, a type of FUS device 225 surrounds the patient's head, as may be used for thermal therapy applied to tissues of or near the brain. The device 225 may have multiple ultrasound transducers for applying focused energy to particular target areas of interest of the head of the patient.

The device 225 can be configured to apply localized energy to heat a targeted region within the area of interest A which includes tissues of or near the brain. As a result, heating may occur in bone tissues, such as that of the skull. The MRI components of the system (including MRI electronics 210) are configured to work within a larger MRI system to acquire magnetic resonance data and for reconstructing images of all or regions of the area of interest as well as temperature-related data. The temperature data may include a temperature at a targeted region and/or a temperature at a reference region. The temperature data may be used to monitor the effectiveness and safety of the thermal therapy treatment and adjust treatment settings accordingly.

The targeted region may include bone tissue, which as described above, has a short $T2/T2^*$. Control of the application of the focused energy via the controller 212 may be managed by an operator using an operator console (e.g., user computer). The controller 212 (which, as shown is also coupled to MRI electronics 210) may also be configured to manage functions for the application and/or receiving of MR signals. For example, the controller 212 may be coupled to a control sequencer such as the control sequencer 152 shown in FIG. 23.

Although the FUS device 225 shown in the embodiment of FIG. 24 utilize ultrasound transducer(s) as the source for delivering localized energy to an area of interest, it should be appreciated that other types of devices may alternatively be used without departing from the patentable scope of the present disclosure. Other possible types of thermal treatment/application devices that may be utilized include laser and/or RF ablation devices, or other devices adapted to heat a target tissue.

Figure 25:
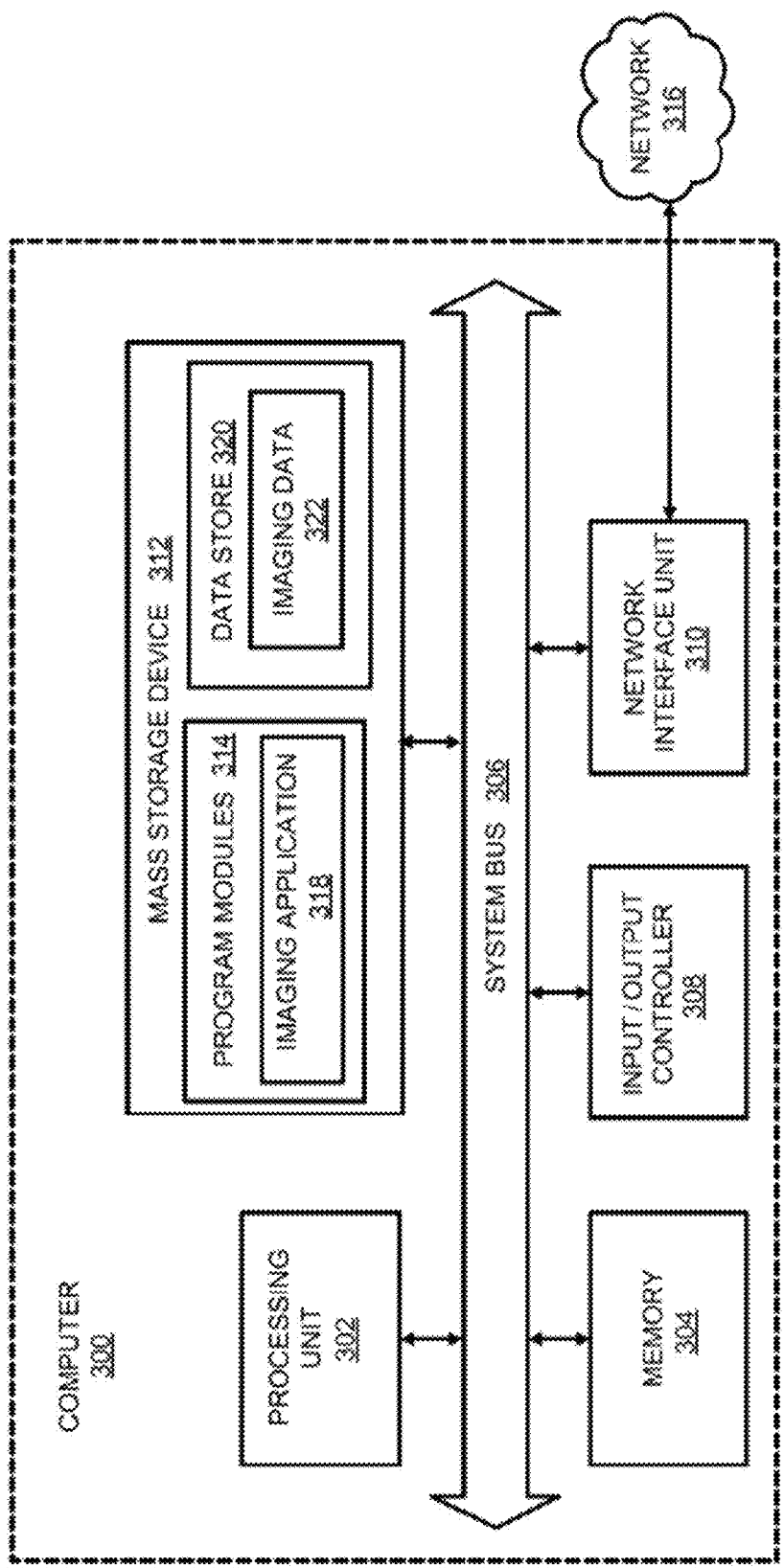
FIG. 25 is a computer architecture diagram showing a computing system capable of implementing aspects of the present disclosure in accordance with one or more embodiments.

FIG. 25 is a computer architecture diagram showing a computing system capable of implementing aspects of the present disclosure in accordance with one or more embodiments described herein. A computer 300 may be configured to perform one or more specific steps of a method and/or specific functions for a system. The computer may be configured to perform one or more functions associated with embodiments illustrated in one or more of FIGS. 1-24. For example, the computer 300 may be configured to perform aspects described herein for implementing the pulse sequences shown and for various aspects of magnetic resonance imaging and related signal and temperature monitoring shown in FIGS. 1-24. It should be appreciated that the computer 300 may be implemented within a single computing device or a computing system formed with multiple connected computing devices. The computer 300 may be configured to perform various distributed computing tasks, in which processing and/or storage resources may be distributed among the multiple devices. The data acquisition and display computer 150 and/or operator console 110 of the system shown in FIG. 23, and the controller 212 and/or MRI electronics 210 of the system shown in FIG. 24, may include one or more components of the computer 300.

As shown, the computer 300 includes a processing unit 302 ("CPU"), a system memory 304, and a system bus 306 that couples the memory 304 to the CPU 302. The computer 300 further includes a mass storage device 312 for storing program modules 314. The program modules 314 may be operable to perform functions associated with one or more embodiments described herein. For example, when executed, the program modules can cause one or more medical imaging devices, localized energy producing devices, and/or computers to perform functions described herein for implementing the pulse sequence shown in FIG. 3, the method shown in FIG. 1, and for various aspects of magnetic resonance imaging and related signal and temperature monitoring and analysis shown in FIGS. 1-24. The program modules 314 may include an imaging application 318 for performing data acquisition and/or processing functions as described herein, for example to acquire and/or process image data corresponding to magnetic resonance imaging of an area of interest. The computer 300 can include a data store 320 for storing data that may include imaging-related data 322 such as acquired data from the implementation of magnetic resonance imaging pulse sequences in accordance with various embodiments of the present disclosure.

The mass storage device 312 is connected to the CPU 302 through a mass storage controller (not shown) connected to the bus 306. The mass storage device 312 and its associated computer-storage media provide non-volatile storage for the computer 300. Although the description of computer-storage media contained herein refers to a mass storage device, such as a hard disk, it should be appreciated by those skilled in the art that computer-storage media can be any available computer storage media that can be accessed by the computer 300.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 300. "Computer storage media", "computer-readable storage medium" or "computer-readable storage media" as described herein do not include transitory signals.

According to various embodiments, the computer 300 may operate in a networked environment using connections to other local or remote computers through a network 316 via a network interface unit 310 connected to the bus 306. The network interface unit 310 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 300 may also include an input/output controller 308 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 300. The input/output controller 308 may be configured to manage output to one or more display devices for displaying visually representations of data, such as display monitors/screens that are integral with other components of the computer 300 or are remote displays.

The bus 306 may enable the processing unit 302 to read code and/or data to/from the mass storage device 312 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 314, which include the imaging application 318, may include instructions that, when loaded into the processing unit 302 and executed, cause the computer 300 to provide functions associated with one or more embodiments illustrated in FIGS. 1-24. The program modules 314 may also provide various tools or techniques by which the computer 300 may participate within the overall systems or operating environments using the components, flows, and data structures discussed throughout this description.

In MRI, the interactions between atomic nuclei are temperature dependent. Thus, MRI is well suited for non-invasive thermometry and is one of the main reasons MR guidance is used for focused ultrasound surgeries. Several MR physics parameters vary with temperature; T1, T2, and the diffusion of coefficient of water all increase, while the resonance of frequency of hydrogen nuclei and proton density (polarization) decreases.

T1 recovery results from dipolar magnetic field interactions between the two hydrogen protons in the same water molecule and also from inter-molecular interactions. To relax from an excited energy state to a lower state, the system must transfer energy at field fluctuations near the Larmor frequency. The field fluctuations are characterized by the frequency spectral density, J(w), which depends on motion as well. For example, free water exhibits fast motion and has a narrow J(w), so its T1 values are long. As with T2, T1 is also dependent on correlation time:

$$\frac{1}{T_1} = \frac{2\gamma^2 B_{loc}^2}{3} \frac{\tau_c(T)}{1+\omega_o^2 \tau_c(T)^2}$$

For most MRI experiments, $\omega_o^2 \tau_c^2 \ll 1$, so that $$\frac{1}{T_1} \propto \tau_c \cdot \tau_c$$

$\tau_c$ is also inversely proportional to temperature, so T1 also approximately increases linearly with temperature within the clinical regime:

$$T = \frac{T_1(T) - T_1(T_{ref})}{m_1} + T_{ref}$$

A difficulty of T1 thermometry is caused by the tissue dependence of $m_1$. Unlike the α constant from PRF which was tissue-independent, $m_1$ has high sample variability. T1 changes for not-fatty tissue are not always reversible, especially if tissue coagulation occurs. However, T2 thermometry also has a variable tissue dependent factor $m_2$.

While T1 is less sensitive to the $B_0$-field of the scanner compared to T2* and does not require a refocusing pulse compared to T2, it is very sensitive to a non-ideal slice profile which occurs when the small flip angle approximation does not apply. If the slice profile is non-ideal, then the T1 measurements can be erroneous. There are some methods for correcting for non-ideal slice profile, but they are still not fully reliable.

While work in T1-weighted thermometry may show promise for some applications, the repeatability of T1-weighted thermometry has not been investigated. T1-mapping has more potential to be repeatable and easier to calibrate, but suffers from requiring more acquisition time compared to T1-weighted thermometry. T1-weighted signal acquired with a volumetric spiral sequence decreases linearly with increasing temperature and can meet the clinical constraints in a repeatable way.

A challenge of T1-mapping is that at least two flip angles of data must be acquired per temperature point doubling acquisition time. Thus, acceleration techniques can be employed to make T1 thermometry viable.

With reference to FIG. 1, a flowchart illustrating steps of a method 100 for performing T1 mapping based thermometry is shown. At step 102, magnetic resonance (MR) data is by a variable flip-angle (VFA) T1 mapping sequence, MR data in an area of interest of a subject. The area of interest of the subject can be any part of the subject's body on which FUS is applied. As a non-limiting example, focused ultrasound (FUS) can be applied to the skull of the subject (i.e. a human patient receiving the treatment), and the area of interest can include corresponding cortical bone of at least part of the skull of the subject that is heated by the application of FUS to treat a selective portion of the brain of the subject. The skull has several important properties relevant for choosing MR sequence parameters. There can be very little water in the skull (which can impact proton density) which can decrease the amount of MR signal available. This can be mitigated using high SNR techniques. Water in the skull exists as free water and bound water. Bound water has a very short transverse relaxation time (T2) on the order of ~100 us. The echo time therefore many need to be on the order of ~100 us as well. Conventional MRI can be too slow to measure the transverse magnetization of bone before it decays away. Therefore a UTE (ultra-short echo time) sequence can be employed (e.g. a UTE sequence originally designed to measure lung tissue). On average, the skull is 5.58-8.17 mm thick, which can require good imaging resolution (e.g. a resolution of 5×5×5 mm). Further, its thickness varies from location to location and between patients. In order to capture skull heating in any location, a large field of view can be used in some embodiments of the present disclosure. For this purpose, a non-selective 3D sequence can be used in embodiments of the present disclosure to achieve a large field of view.

For temporal constraints, the skull's bone can be similar to a ceramic material functioning as a thermal insulator preventing heat flow from the scalp into the brain and vice versa, and it has a cooling time constant estimated to be on the order of minutes. Therefore, the temporal resolution should be short compared to the cooling time of the skull, for example some embodiments of the present disclosure can achieve a temporal resolution of 90 s or less. A table of values showing non-limiting examples of design/clinical parameters is shown in FIG. 2, including the above skull parameters and other design constraints of MRI-based thermometry.

Still with reference to FIG. 1, the MR data in step 102 can include a plurality of T1 values over time that include a first point in time and a second, later point in time, where the acquisition of the MR data comprises applying an accelerated three-dimensional (3D) ultra-short (UTE) spiral acquisition sequence with a nonselective excitation pulse, and where the acceleration of the accelerated 3D UTE spiral acquisition sequence comprises the use of at least one of partial kz acquisition and variable density of spiral interleaves.

As a non-limiting example, the acquisition of MR data can be performed using the UTE VIBE sequence, which is illustrated in FIG. 3. The UTE VIBE sequence is a spoiled GRE sequence suitable for T1-based contrast imaging and is ultimately very fast. An alternative sequence that can be used in some embodiments of the present disclosure is the AWSOS (acquisition-weighted stack of spirals) sequence which uses a stack of spirals to accelerate in-plane data collection, variable-duration slice encoding, and a movable spiral readout achieving an echo time of 608 us. Differences between UTE VIBE and AWSOS include that the UTE VIBE is non-selective with a rectangular RF pulse, and the min TE is less than 100 us. The UTE VIBE sequence was developed for breath-hold UTE lung imaging. UTE VIBE has the following advantages for bone thermometry: (1) an ultra-short echo time limited only by the duration of a rectangular pulse; (2) a spiral readout enabling a highly efficient short readout duration which starts at the center of k-space; (3) non-selective (3D) excitation. While the present disclosure refers to UTE VIBE as an exemplary sequence, it should be understood that the use of other sequences is contemplated by the present disclosure.

The signal model is given by the GRE equation:

$$M_{xy} = S = M_o(T)\sin(\alpha)\frac{1 - e^{-T_R/T_1(T)}}{1 - \cos(\alpha)e^{-T_R/T_1(T)}}e^{-TE/T_2^*(T)} \qquad \text{Eq. 1}$$

where $M_{xy}$ is the measured signal; $M_o$ is the thermal equilibrium magnetization; $\alpha$ is the flip angle; and $T_R$ is the repetition time. The $e^{-T_R/T_1(T)}$ term provides the T1-weighting on the signal. If the TE is sufficiently short, then the $e^{-TE/T_2^*(T)}$ term is negligible. T1 can then be estimated by using linear least squares fitting on Eq. 1 from signal from two flip angles. The two optimal flip angles are calculated by using propagation of errors to minimize an expression of uncertainty in quantitative VFA T1 mapping occurring when the signal is 0.71 of the Ernst angle signal (maximum signal).

There are at least two ways to attain a short RF: using half-sinc excitation or using a rectangular, non-selective pulse. However, if using half-sinc excitation, two half-sinc RF pulses are needed to achieve a good slice profile doubling scan time. UTE VIBE can attain a 120 us rectangular pulse for a 35° flip angle (shorter for lower flip angles). The echo time with this kind of pulse is calculated from the center of the rectangular pulse with 20 us for switching the coil from transmit to receive leading to a minimum 80 us TE (60 us+20 us). The center of the rectangular pulse represents the average amount of T2 decay over time. The sequence also has an RF spoiler which prevents coherences from previous TR (stored in Mz) from contributing to the current TR's signal.

The $G_z$ spatial encoding is one of the strengths of this sequence in minimizing echo time. Z-information is phase-encoded with a $G_z$ gradient after the RF pulse and before the readout spiral. Each TR corresponds to a selected k-z plane in k-space, so that the third dimension is sampled traditionally in the Cartesian way, whereas k-space in $k_x$, $k_y$ dimensions is sampled using spirals. Thus, the sampling trajectory is a stack of spirals. The duration of the $G_z$ gradients starts at 0 us for kz=0 and increases to the maximum duration set by the desired z-resolution. The variable duration of the $G_z$ gradient leads to a variable echo time.

The echo time depends on the length of the $G_z$-phase encode gradient and is thus variable as described above and shown in FIG. 4A. Minimum echo time (minTE=50 us) occurs when there is no $G_z$ gradient (at the center of kz space); the readout spirals are played immediately after the RF pulse. For a non-limiting example embodiment of the UTE VIBE, the maximum echo time is 373 us for the highest kz plane of data. Because most of the signal energy comes from the center of k-space, the effective echo time is close to the minimum echo time. However, variable echo time leads to blurring as the longer echo time corresponds to more T2-decay (attenuation) of the higher spatial frequencies (FIG. 4B), in which the signal depends on the echo time, as described originally by Qian et al:

$$S(t_d) = S(0)\exp\left(-\frac{t_d - t_{d,min}}{T_2}\right)$$

where $S(TE(k_z))$ is the signal intensity after a z-encoding of duration $t_d$.

Figure 5B:
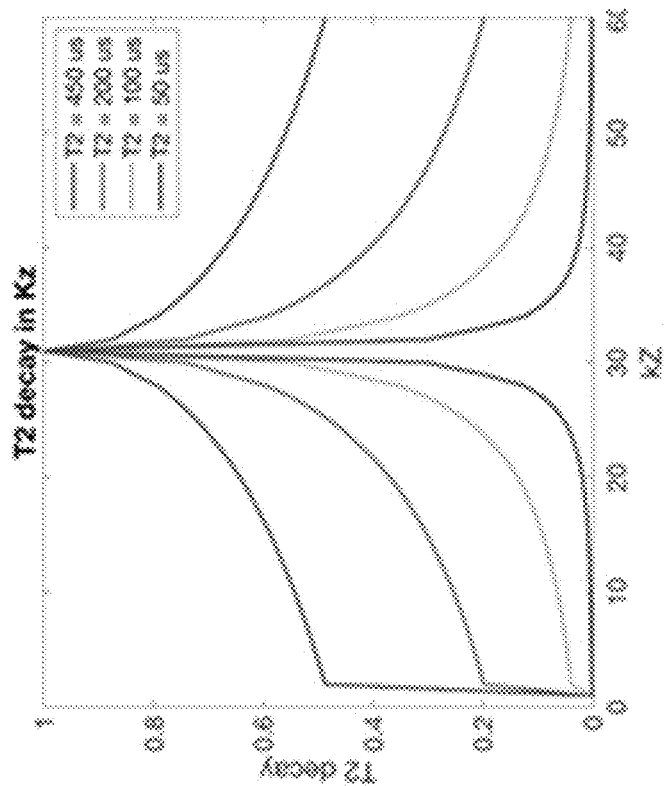
Figure 5A:
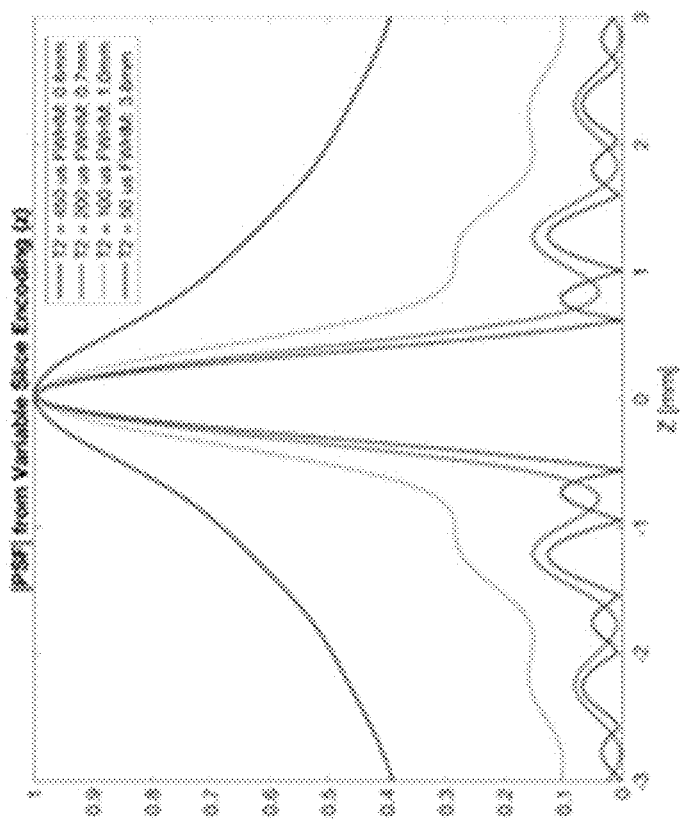

For species with a T2 of 450 us, a blur of 0.6 mm is predicted to occur for UTE VIBE which meets the goal for human imaging and this blur is illustrated in FIGS. 5A-5B.

Figure 6:
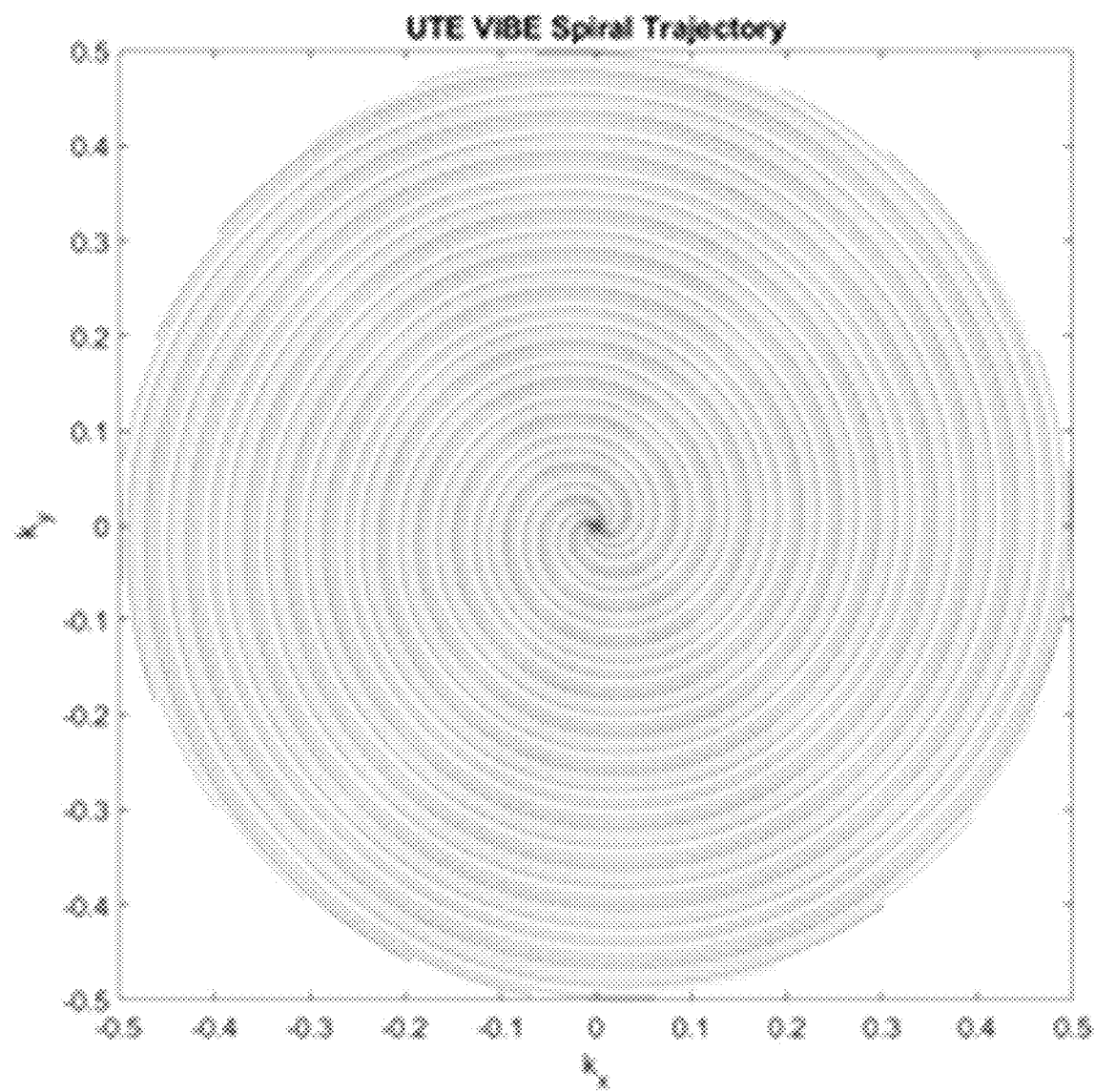
FIG. 6 illustrates a non-limiting example of a UTE VIBE K-space Trajectory. Uniform spiral density.

Though spirals can be technically difficult to implement on a scanner, can require special reconstruction techniques, and can be sensitive to off-resonance, they have many advantages, such as (1) reducing acquisition time due to efficient k-space coverage; (2) having a large SNR by starting acquisition at the center of k-space, which is also an advantage for ultra-short echo time sequences; (3) being robust against motion in dynamic MRI; (4) allowing real-time MRI with high in-plane resolution; and (5) being less sensitive to aliasing. For these reasons, spirals are a viable option for bone thermometry, which requires ultra-short echo time, high SNR, and rapid image acquisition. The k-space spiral trajectory as implemented in a non-limiting example of an MRI scanner that can be used in an embodiment of the present disclosure is shown in FIG. 6.

Blurring from spiral sampling during readout can occur due to different amounts of T2 decay modulating the $k_x$, $k_y$ signal in the spiral trajectory:

$$S(k_x(t),k_y(t),k_z(t)) = e^{-t/T^*2} \iiint p(x,y,z) e^{-j(x*k_x(t)+y*k_y(t)+z*k_z(t))} dxdydz$$

Figure 7:
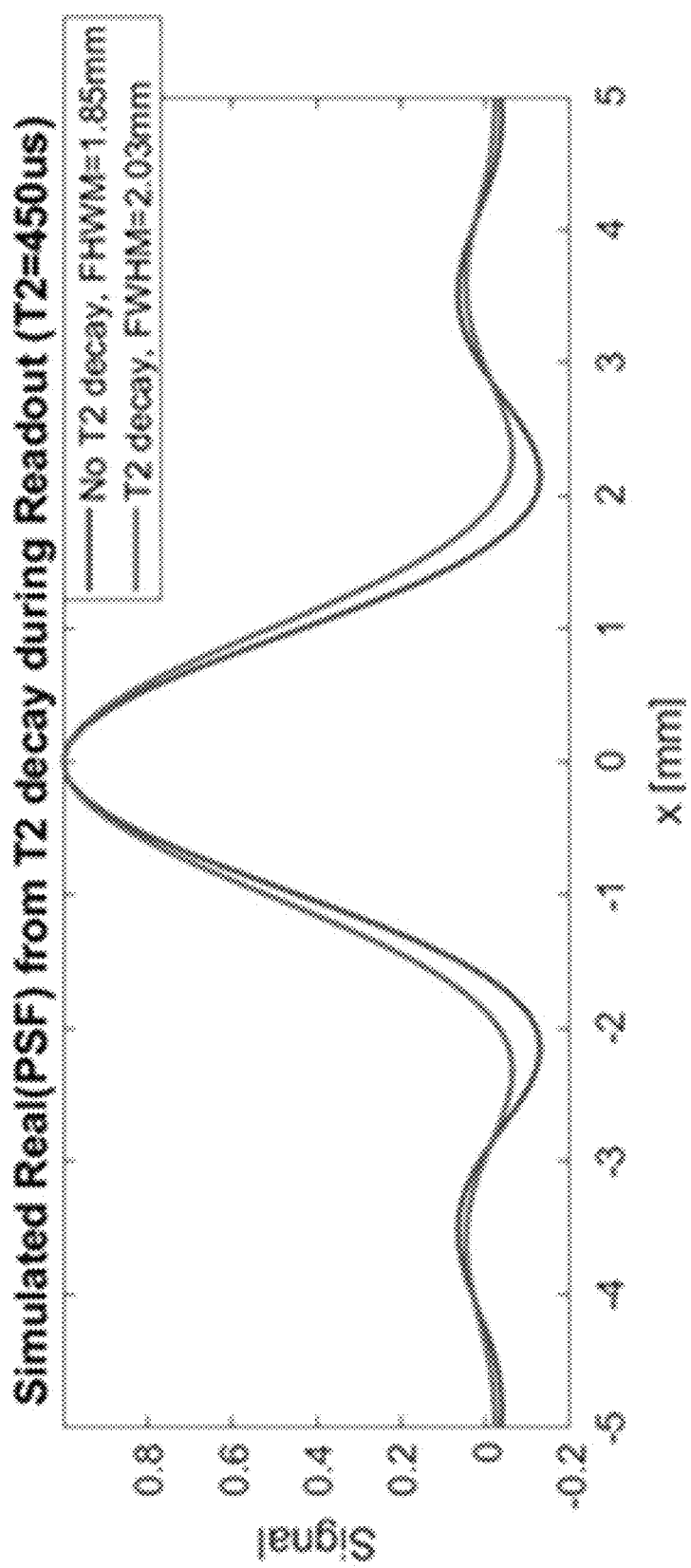
FIG. 7 illustrates the effect of T2 decay during readout.
Figure 8:
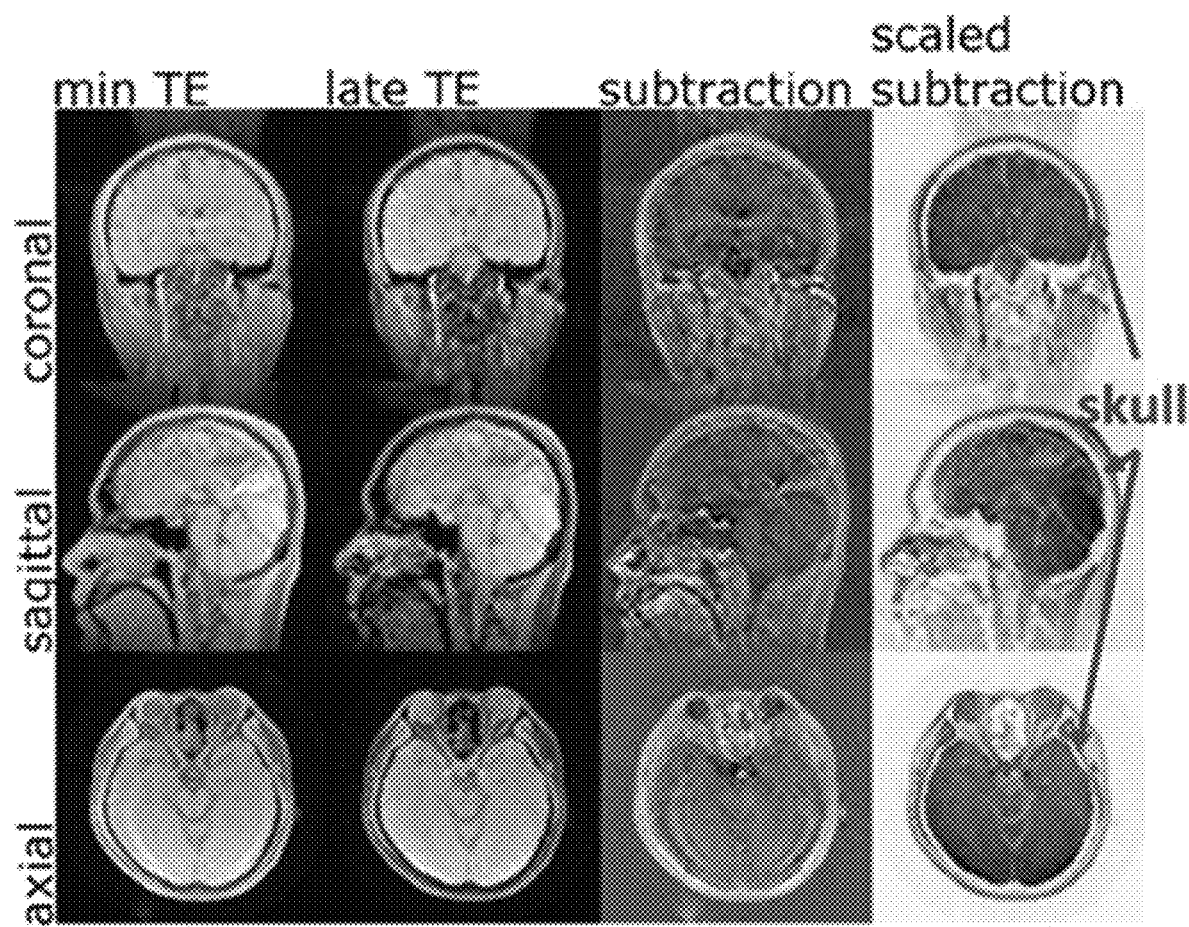
FIG. 8 illustrates an example of whole-head in-vivo UTE data acquired in 67 seconds. TR=10 ms. TE=50-370 us. Flip angle 5°. FOV 240 mm3. Resolution (2.5×2.5×3.75 mm3). 98 interleaves of 1.0 ms duration each; 67-seconds acquisition time. Imaging was performed using a 12-channel head RF coil. The second image was obtained at TE of 5.1 ms for late-TE comparison.

In the case for a T2* of 450 us, there FWHM changes from 1.85 mm (no decay) to 2.03 mm (9.73% difference). This effect is illustrated in FIG. 7, which illustrates the effect of T2 decay during readout.

Figure 9:
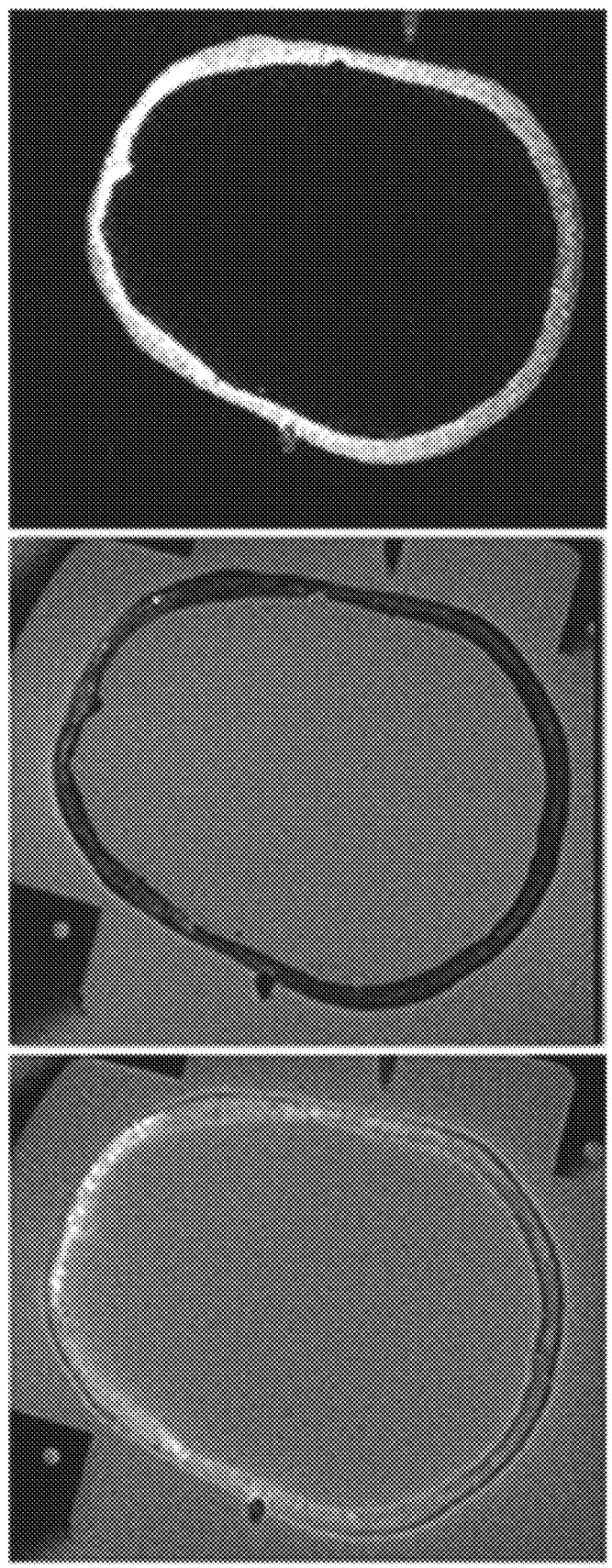
FIG. 9 illustrates ex-vivo skull high-resolution UTE data. TR=11 ms. $TE_{min}$=50 us. Flip angle 20°. FOV 333×333×154. Resolution (0.8 mm3). X interleaves of 0.5 ms duration. 29-min. acquisition time. Imaging was performed using a Tx/Rx CP Head Coil. The second illustration corresponds to data obtained at TE of 2.5 ms for late-TE comparison.

The UTE VIBE has the advantage of imaging a large volume (240 mm³) under 90 s (FIG. 8) making it rapid enough for skull thermometry during MRgFUs. For comparison, FIG. 9 illustrates MR data acquired from an ex vivo skull at high resolution.

Though T1-mapping thermometry can take twice as long as T1-weighted thermometry, the T1 vs. temperature trend is much more reliable and linear. By using the advantages of spiral MRI, it is possible to accelerate T1-mapping to meet the clinical constraints (e.g. the non-limiting constraints illustrated in FIG. 2).

Again referring to FIG. 1, the MR data acquisition sequence used in step 102 can be accelerated to conform to clinical constraints (e.g. the constraints shown in FIG. 2). In some clinical settings, it is desirable that the thermometry of a patient's head in the water bath should not take more than 90 s. FIG. 2 shows a resolution of as a target, (<5×5×5 mm), however, embodiments of the present disclosure are capable of higher resolutions (e.g. 1.9×1.9×5 mm), as it is desirable to have a resolution high enough to develop a satisfactory image of a an average skull, which has an average thickness of 6.5-7.1 mm. To achieve the 90 s goal for two flip angles, the time per kz-encoding (200/5=40 kz encodings in total) can be 45 s/40=1.13 s per kz encode. Temporal resolutions different than 90 s are contemplated by the present disclosure, and it is therefore contemplated that the time per kz-encoding can be different than 1.13 s per kz encode in different embodiments of the present disclosure.

The acceleration method can be any suitable acceleration method that can generate T1 mapping information within the desired clinical constraints. For example, partial Fourier imaging can be applied. Partial Fourier imaging takes advantage of the conjugate symmetry of k-space applicable when the object is real or there are no phase errors, where $|k(x,y)|=|k(-x,-y)|$ and $\varphi_{x,y}=-\varphi_{-x,-y}$ (same amplitude, opposite phase). In theory, only half of k-space needs to be acquired, but in practicality, phase errors do occur from $B_0$-field inhomogeneities, concomitant gradients, and eddy currents. Thus, partial Fourier sampling can require acquisition of 60% or more of k-space. For UTE VIBE, ⅝ kz partial Fourier sampling was selected as a non-limiting example, and therefore the bottom 25% of k-space was not collected and scan time was reduced by approximately 25%.

Another non-limiting example of an acceleration technique that can be used is variable density spiral design. Variable density spiral design samples the center of k-space at the Nyquist limit but under-samples the outer k-space regions reducing acquisition time. Because the center of k-space is fully-sampled and can contain most of the energy, under-sampling in outer k-space can lead to fewer artifacts than under-sampling uniformly. As spiral aliasing results in blurring instead of replicant overlap, under-sampling in the high spatial frequencies can lead to benign artifacts.

Again with reference to FIG. 1, step 104 includes determining a temperature change in the cortical bone based at least in part on a mathematical relationship established by T1 mapping thermometry produced according to the T1 mapping sequence. The temperature change in the cortical bone that occurs between the first point in time and the second point in time, can be determined, where the temperature change is caused at least in part by a change in the FUS.

Conventional MR thermometry does not work in the skull due to its ultra-short T2, so T1-based thermometry is used. Skull thermometry imaging should be relatively fast to capture temperature changes in clinically relevant timescales (e.g. the 90 s timeframe illustrated in FIG. 2). It is also beneficial for skull thermometry to be volumetric in order to detect heating anywhere in the skull, and have a short echo time (<100 us) to enable the imaging of bone. T1 is linear with temperature in cortical cow bone and can thus be calibrated to temperature. However, existing methods have not been demonstrated under clinical constraints and have a long acquisition time (8 minutes).

Though T1-mapping thermometry can require twice as many acquisitions as T1-weighted thermometry, the T1 vs. temperature trend should be much more reliable and linear. By using the advantages of spiral MRI, it is possible to accelerate T1-mapping to meet the clinical constraints (e.g. the constraints in FIG. 2).

Figure 10B:
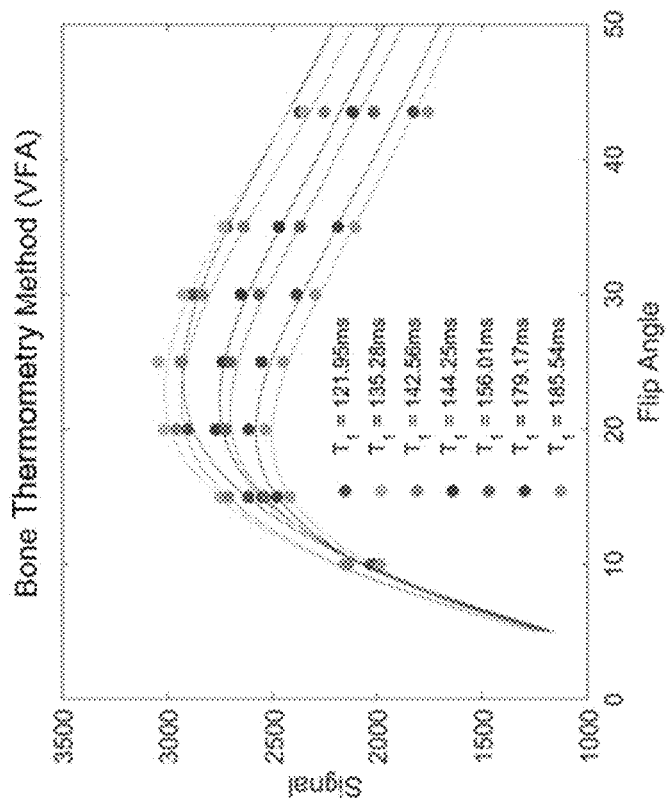
Figure 10A:
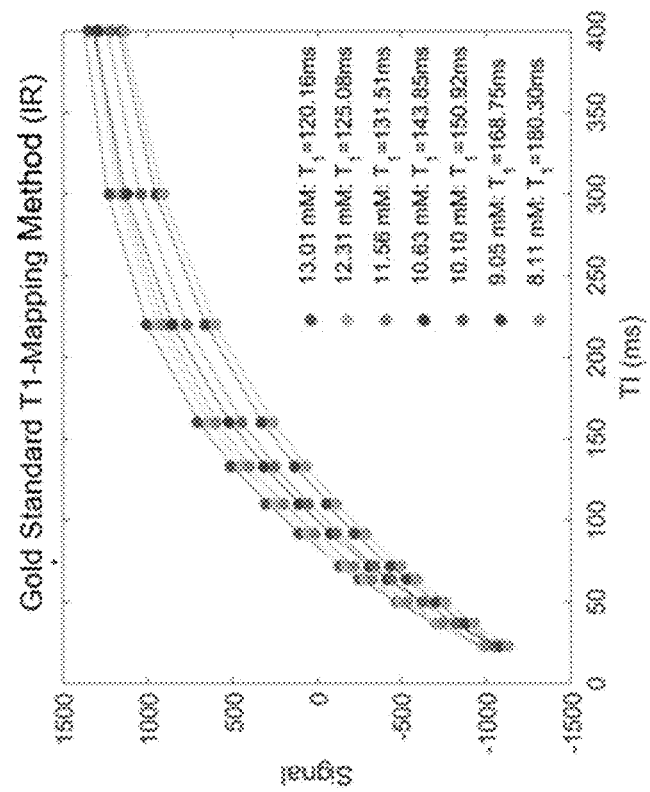
Figure 10C:
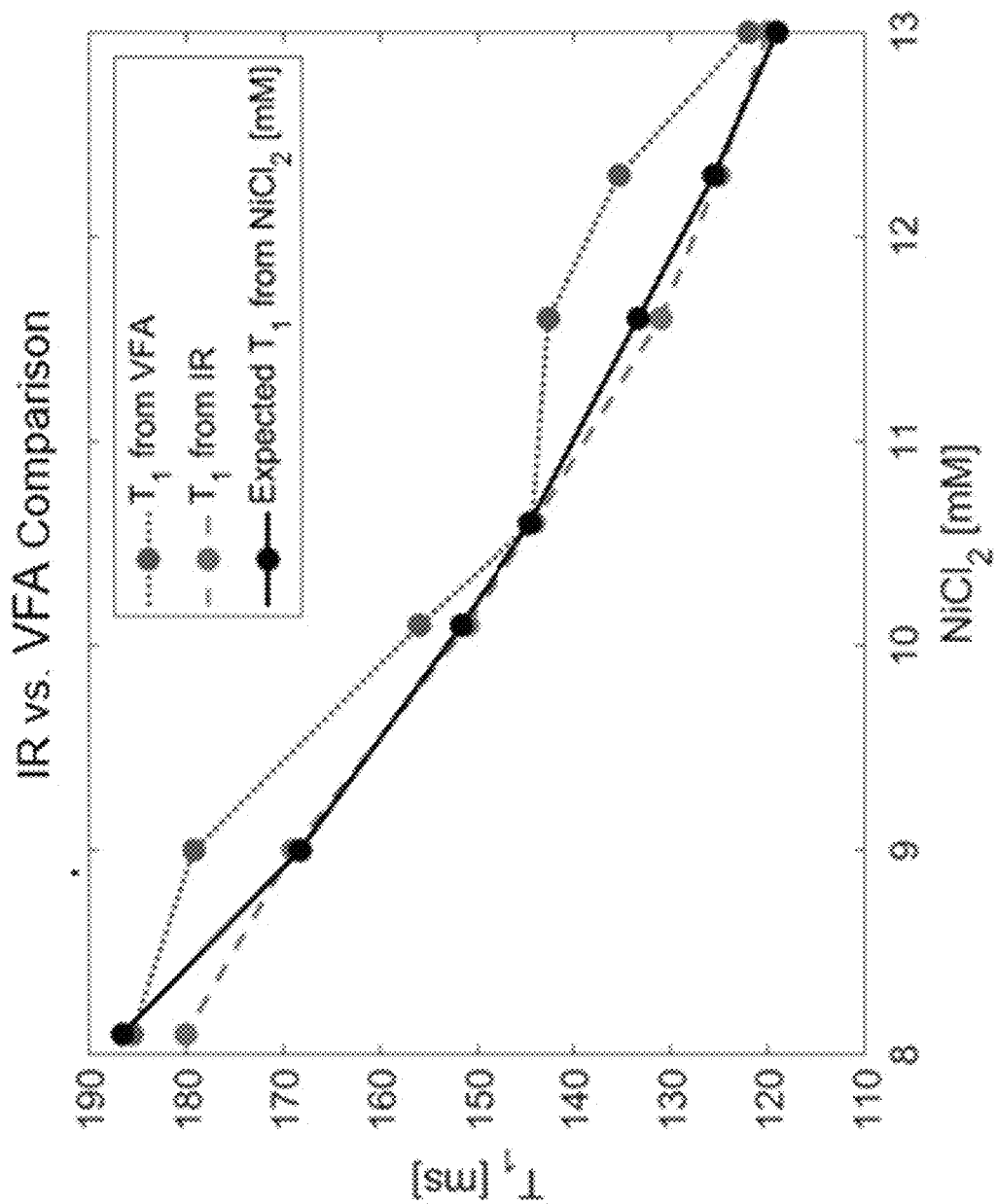

$T_1$ values from the UTE VIBE VFA method and the IR method were compared in FIGS. 10A-10C. The IR values (shown in FIG. 10C in solid black) were much closer to the expected $T_1$ based on $NiCl_2$ concentrations (mM). The mean difference in $T_1$ between VFA and IR was 6.39 ms (4.46% difference). The VFA values illustrated in FIG. 10C (blue solid line) are less linear. However, IR may not be practical for UTE imaging; in IR, a 180° magnetization inversion must be achieved. Materials with short T2 such as cortical bone undergo relaxation during the inversion pulse thus making IR inefficient. The noisy VFA-T1 measurements can be corrected by performing a $B_1$ map to measure the actual flip angles rather than relying on the potentially erroneously prescribed flip angles. Overall, the UTE VIBE VFA method can be sensitive to $T_1$ with 5% error, enabling T1-mapping thermometry of cortical bone in step 104. This T1-mapping thermometry has several useful clinical applications, including allowing the person or system administering FUS to a patient to either increase or decrease the intensity of the FUS and therefore determine the optimal level of FUS to apply to a patient to both treat the patient's condition and avoid unintentional damage to the surrounding tissue.

The techniques described herein can be applied to portions of the brain that correspond to diseases including Parkinson's disease, essential tremor, neuropathic pain, depression, and obsessive-compulsive disorder, although the use of FUS to treat other conditions, while using T1 mapping thermometry, is contemplated by the present disclosure.

EXAMPLE IMPLEMENTATIONS AND CORRESPONDING RESULTS

The following description includes discussion of example implementations of certain aspects of the present disclosure described above, and corresponding results. Some experimental data are presented herein for purposes of illustration and should not be construed as limiting the scope of the disclosed technology in any way or excluding any alternative or additional embodiments.

First, T1-weighted thermometry was tested in simple conditions (cooling of bone in a water bath) and then in more challenging and clinically relevant conditions (heating of bone by focused ultrasound).

The variable results of T1-weighted thermometry are a potential disadvantage compared to T1-mapping thermometry, which depends on less factors and assumptions but can take longer. T1-mapping with a better coil and increased resolution was also investigated. Analyzing both the T1 values and the T1-weighted signal at different flip angles, it was observed that the trend in T1-weighted signal is highly dependent on flip angle. Also, even with higher flip angles, T1-weighted signal is not fully linear with temperature. For the same ROIs, T1-mapping results showed a consistent linear trend (0.98+/−0.15 ms/° C.) whereas T1-weighted results showed mixed results. Thus, T1-mapping with the UTE VIBE was observed to be reliable, linear, and potentially able to be calibrated to indicate skull temperature. However, in clinical settings it is desirable to accelerate T1 mapping. To accelerate T1-mapping, a ⅝ partial kz sampling was used and the sampling density of the spiral interleaves was changed using linear variable density with full sampling (1) at the center of k-space and 0.7 at the edge of k-space. The under-sampled T1 of bone cooled in a water bath still showed linear results, though the slope was higher than the fully-sampled T1 of other bones. Under-sampled T1-mapping was also done in ex-vivo human skull with results highly dependent on ROI due to the thinness of the skull and relatively coarse resolution.

UTE VIBE T1 mapping thermometry is promising in its clinical applicability to skull monitoring, as preliminary results have shown linear measurements of T1 with temperature in contrast with the variable results of T1 weighted thermometry.

Figure 11B:
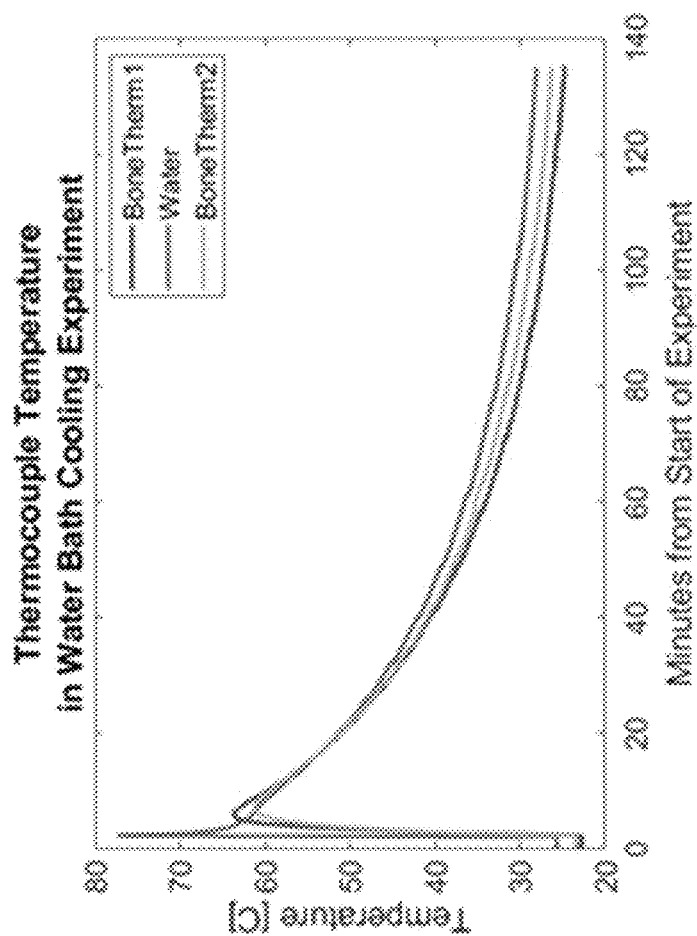
Figure 11A:
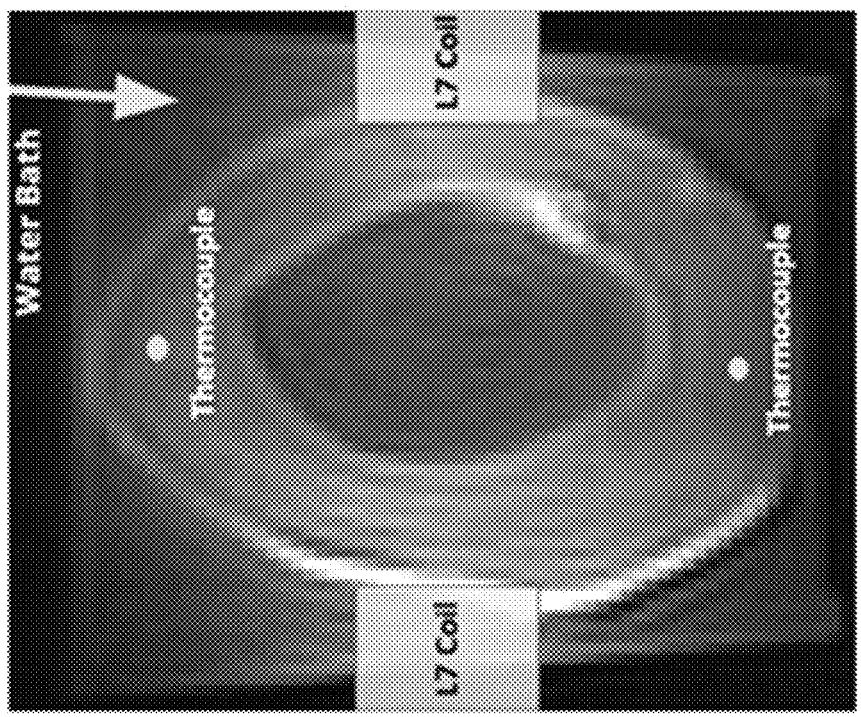

An embodiment of the present disclosure was tested by heating and cooling bone samples in a water bath, and non-limiting examples are described herein. To test T1-mapping thermometry, several trials both with heating bone and cooling bone in a water bath were conducted. In cooling experiments (e.g. experiments 1 and 2 illustrated in FIGS. 13A-13B), cortical bovine bone was placed into a small plastic container filled with water heating to ~70° C. and equilibrated for 10 min. The long axis of the bone was aligned with the scanner and imaged transaxially with an L7 coil as it cooled with an improvement in SNR due to the proximity of the coil to the sample. (FIGS. 11A-11B).

Figure 12A:
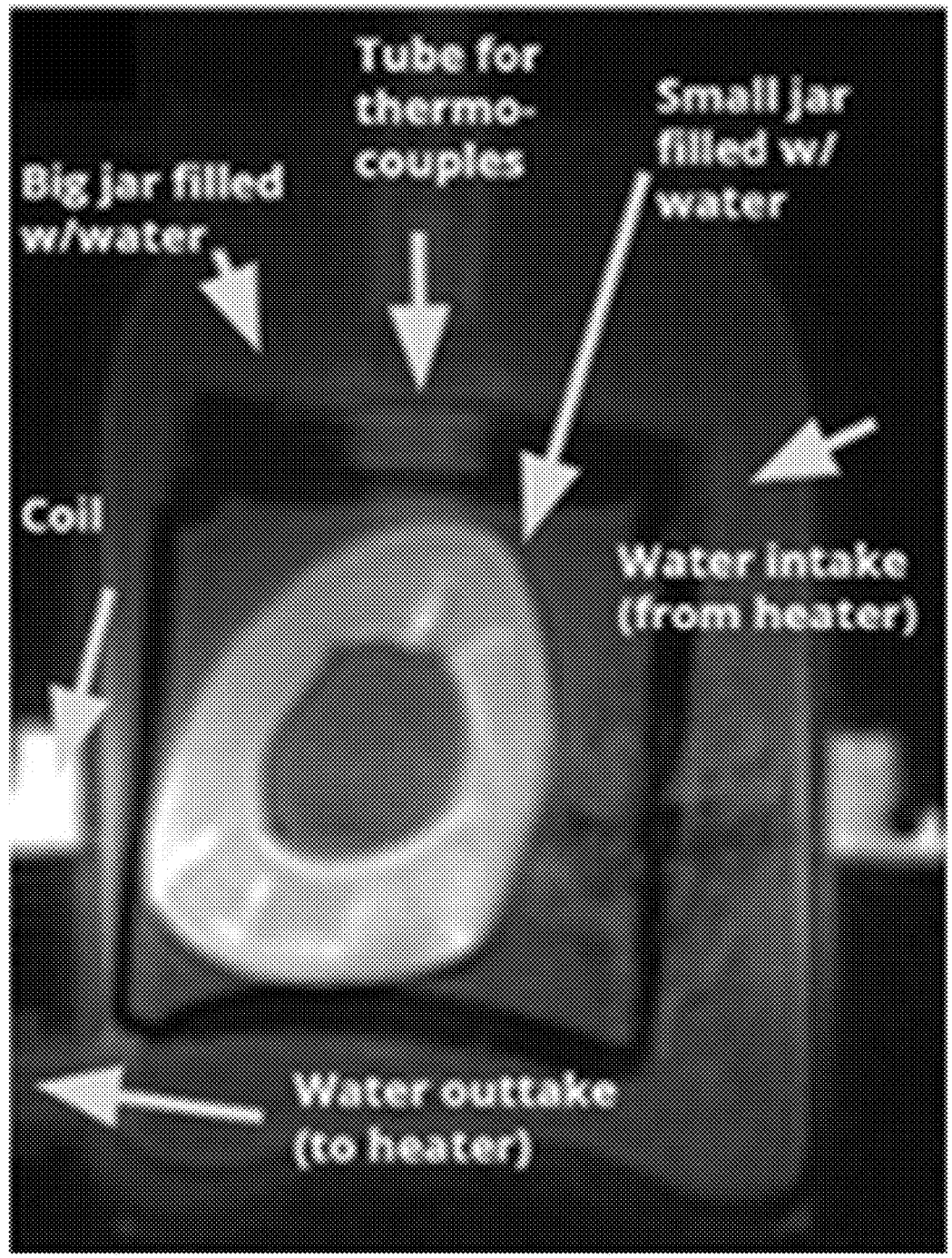
Figure 12B:
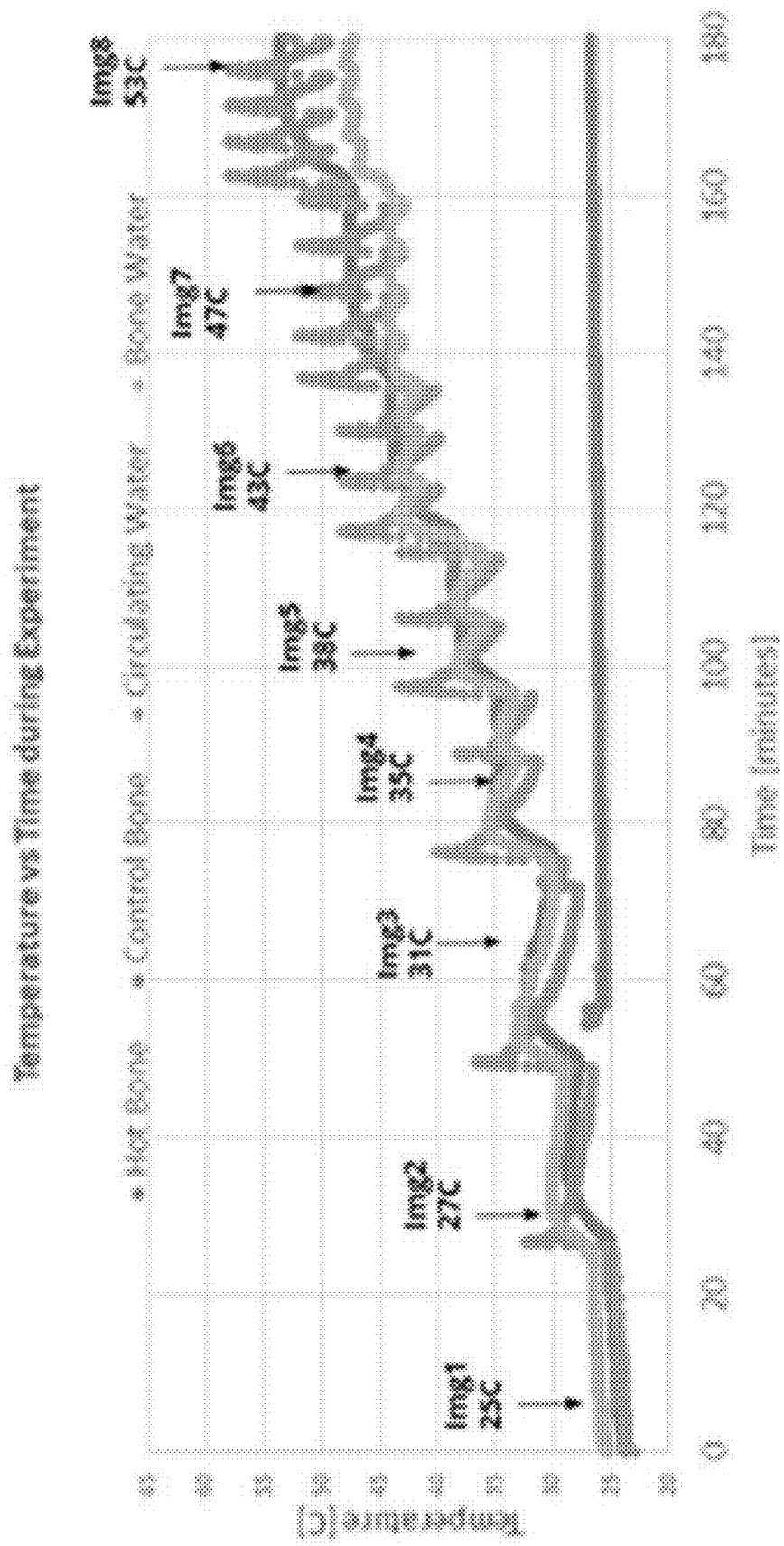

Hysteresis of bone heating was tested by imaging the bone during heating using a water heater and a pump to see whether the change in T1 during heating was comparable to the change in T1 during cooling. A custom setup was used as shown in FIG. 12A. The bone was placed into a small jar closed off from the outer jar. The circulated water was heated from room temperature up to 53° C. in ~4° C. increments. The bone and water in the small jar slowly heated in response to the surrounding water leading to gradual temperature changes (yellow trend slowly increases compared to the grey spikes of the circulating water in FIG. 12B. In order to fit the small bone jar, a drill press was used to cut the bone into a smooth round shape which allowed it to fit into the jar.

Figures 13A, 13B:
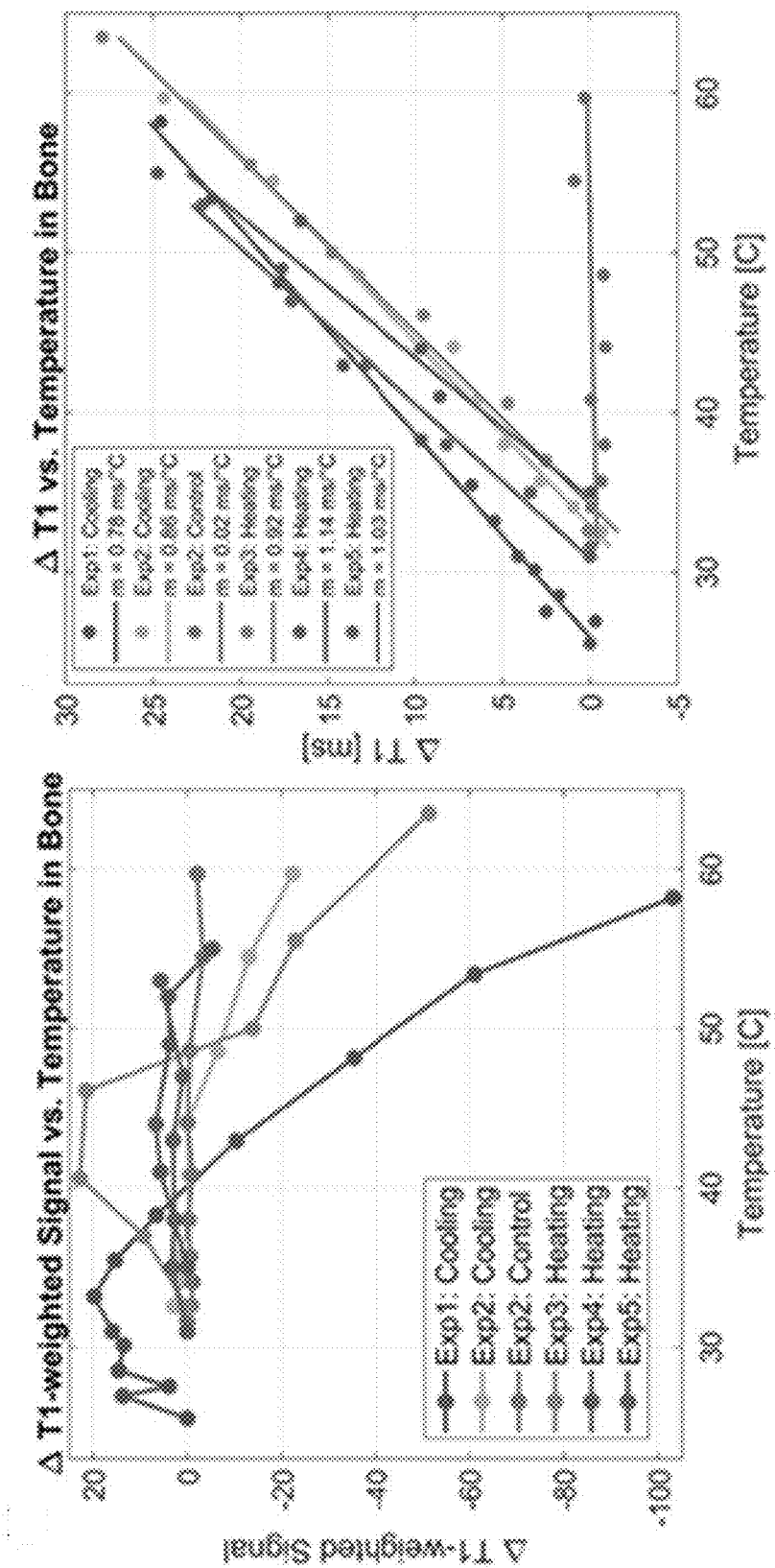

In heating experiments, bovine femur bone was placed into a small jar closed off from the outer jar. The circulated water was heated from room temperature up to 53° C. in ~4° C. increments. The bone and water in the small jar slowly heated in response to the surrounding water leading to gradual temperature changes. The T1-weighted signal (at 35° flip angle) are shown in FIGS. 13A-13B. The T1 measured from the same ROI (same color) using two flip angles from the VFA method are also shown, illustrate the relationships between different T1 signals and temperature in bone for various experiments, wherein FIG. 13A illustrates the relationship between changes in T1-weighted signal vs. temperature in bone, and FIG. 13B illustrates the relationship between a change in T1 vs. temperature in Bone. Though the T1-weighted signal is nonlinear, the corresponding T1 vs temperature values are linear, increasing with temperature (average slope of 0.98+/−0.15 ms/° C.), which is comparable to Han et al.'s result of 0.84 ms/° C. measured using a slower 3D radial UTE pulse sequence.

Figure 14A:
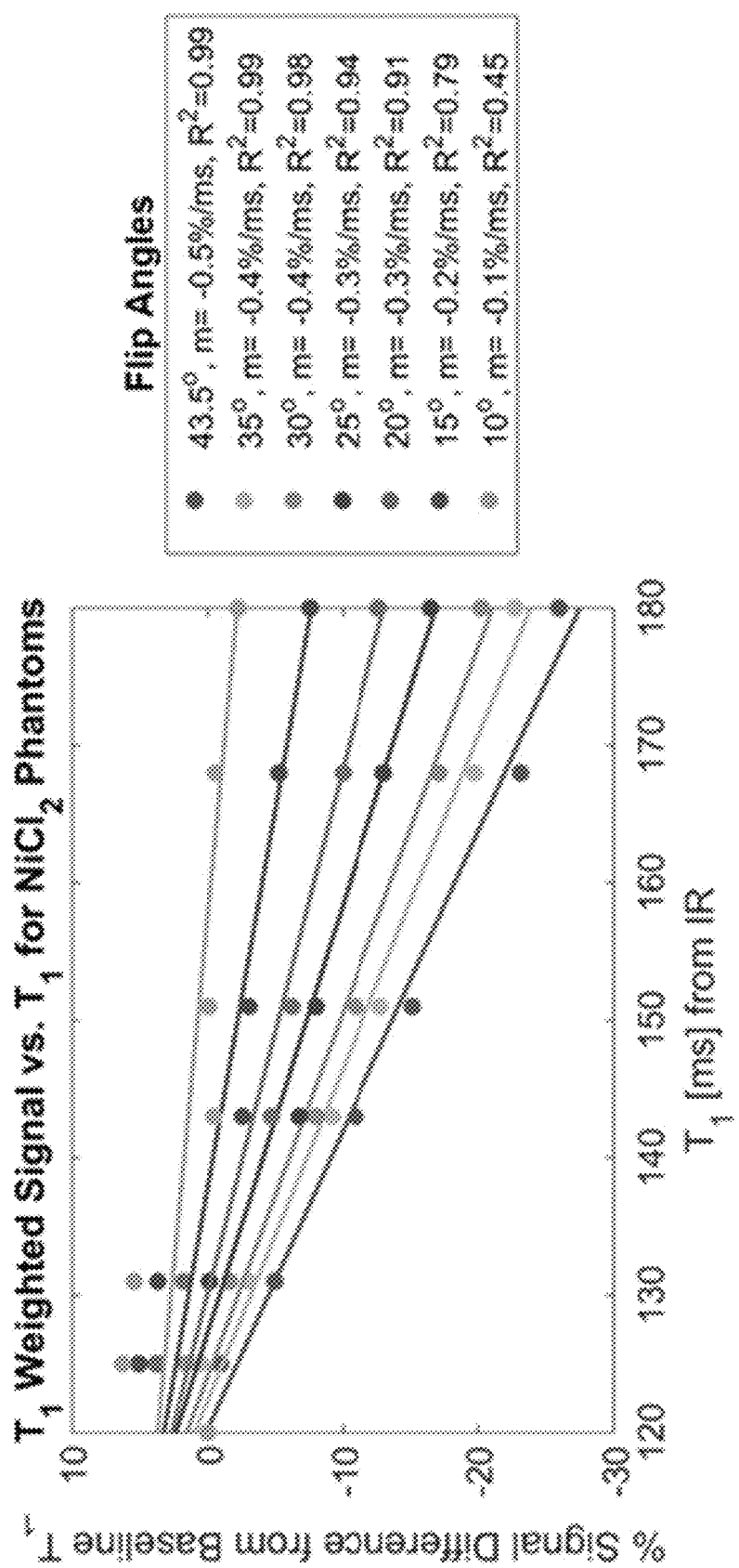
FIGS. 14A-14B illustrate experimental results.
Figure 14B:
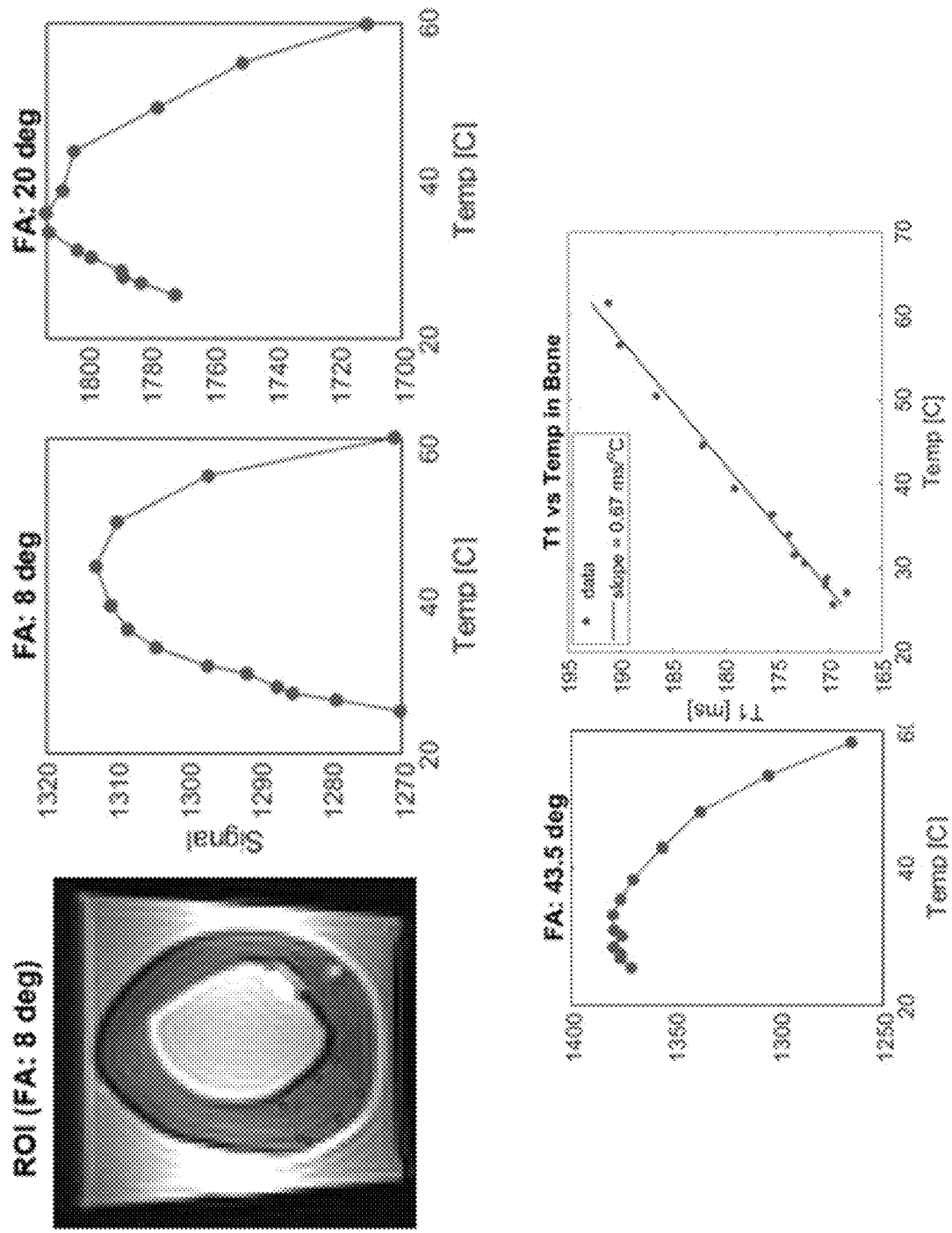

Ex-vivo bovine femur bone was placed in a container of hot water and imaged as it cooled with a thermocouple measuring temperature in the bone. The signal was measured for three different flip angles (8°, 20°, 43.5°) at each temperature point. As $T_1$ increases with temperature, the $T_1$ weighted signal should decrease linearly in accordance to Eq. 7 for all flip angles. As shown in FIG. 14A, the 8° FA data would show a smaller slope compared to the 43.5° FA. However, in the results illustrated in FIG. 14B, a mix of trends was observed.

Figures 15A, 15B:
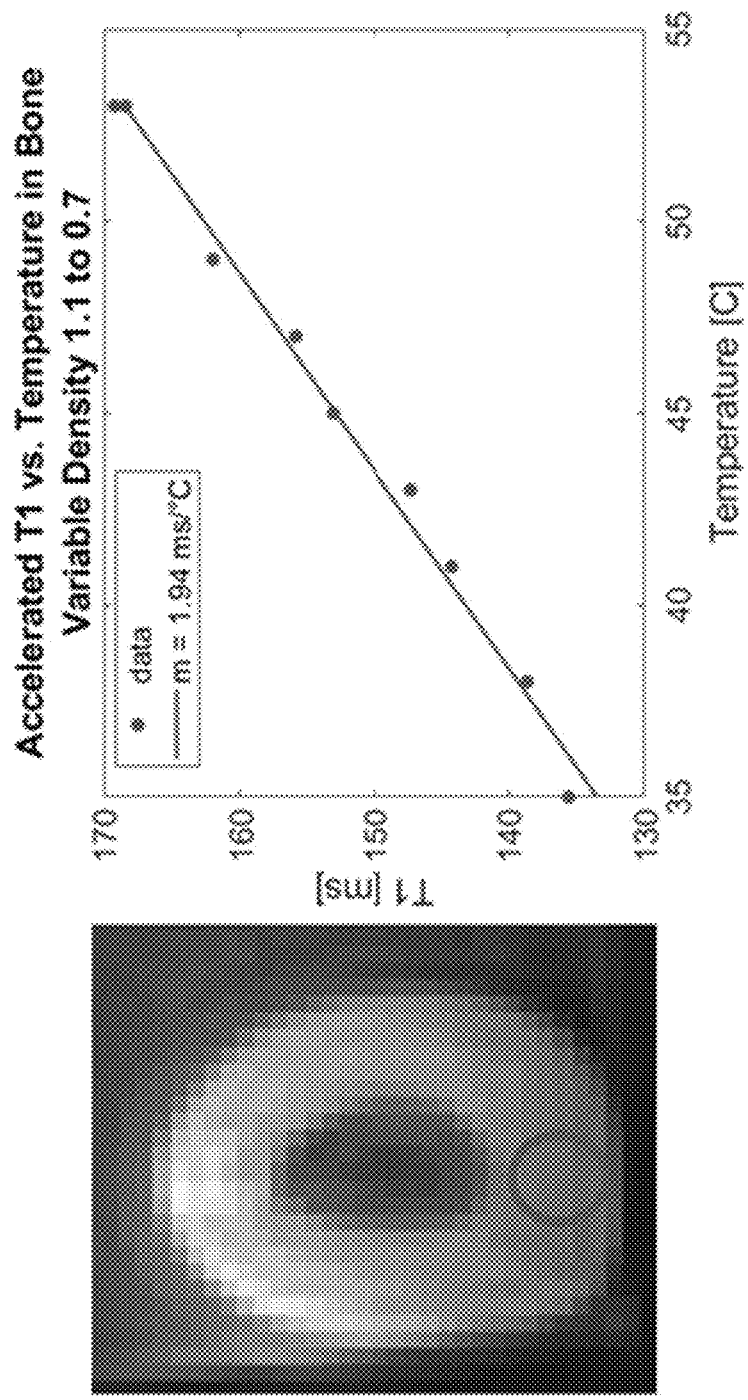

A cooling experiment was conducted using an embodiment of the present disclosure for cow bone cooling in a water bath with an under-sampled UTE VIBE sequence. A linear variable density was chosen (1.1 to 0.7) with ⅝ partial kz, 105 interleaves, (1.625, 1.625, 5 mm) resolution lead to a 1.11 s/kz-encode time (<90 s for two flip angles). A linear T1 trend was observed with reasonable bone T1 values (FIGS. 15A-15B). Previous sequences had a TA of 7.71 s/slice with higher resolution; an acceleration by ~7 times still allows for a measurement of linear T1 changes. Thus, T1-VFA based thermometry is feasible with spiral variable-density acceleration. The slope of T1 vs. temperature for this under-sampled bone image is much higher than previous measurements (averaging 0.98 ms/° C.). The effect of under-sampling on the measured change of T1 with temperature in cow bone remains to be investigated and would provide insight on how under-sampling may affect the calibration of T1 changes with temperature.

Figure 16A:
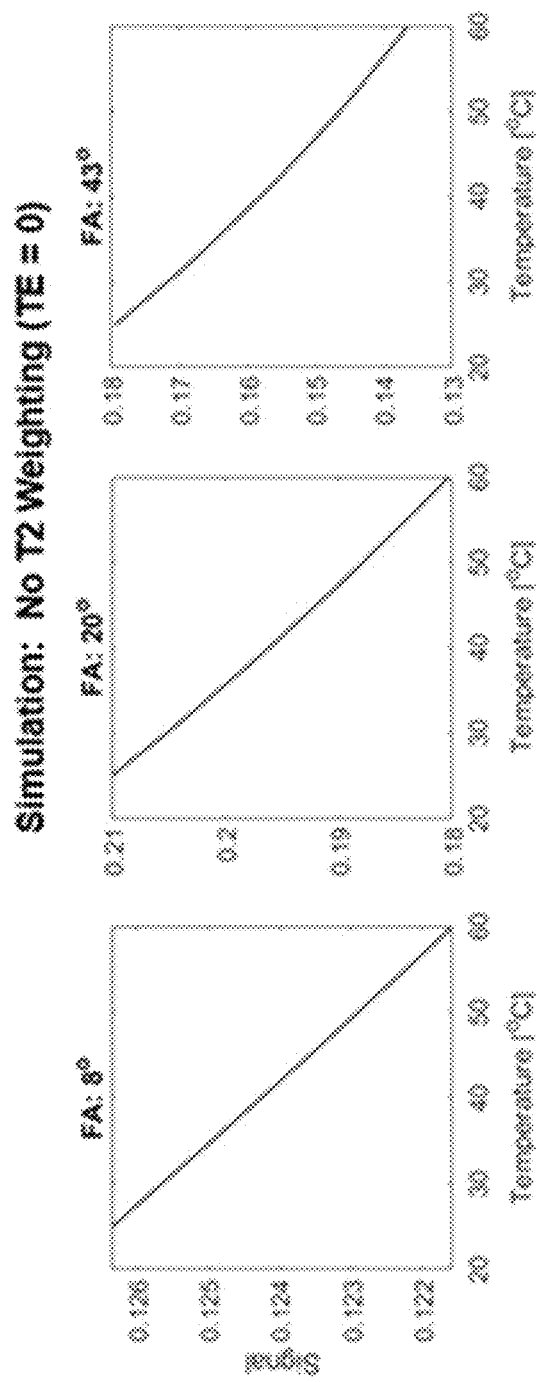
Figure 16B:
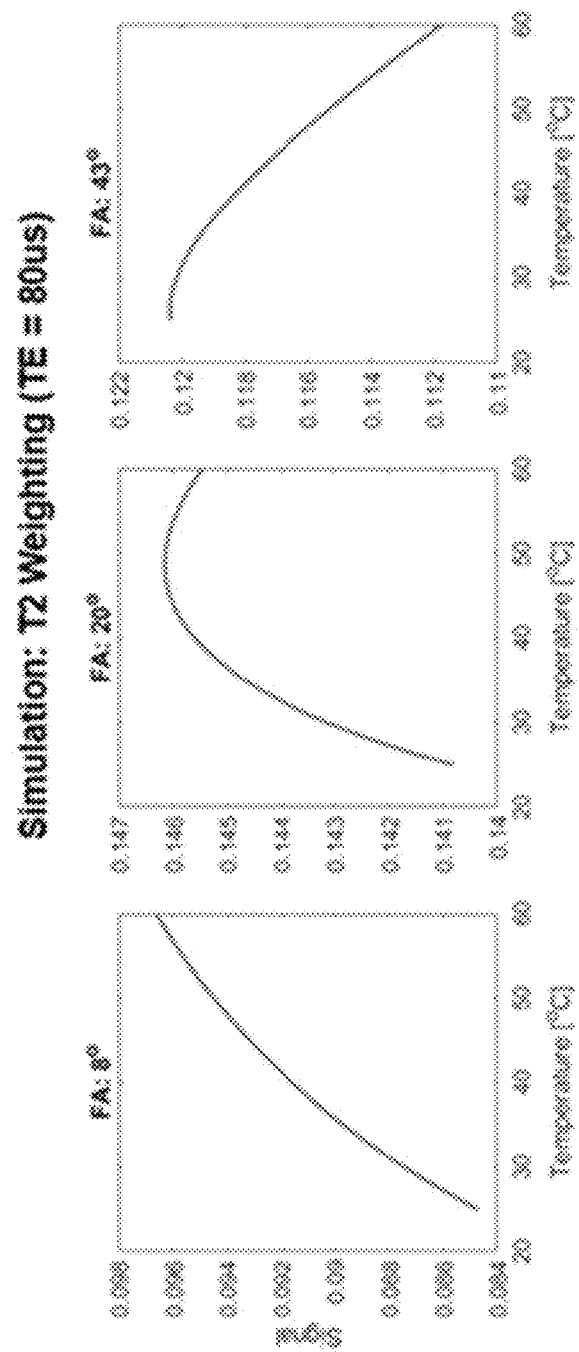

It appears that even though a UTE (TE=80 us) sequence was used, there may be significant amount of T2 weighting dominating at lower flip angles (FA: 8°) and being less prominent but still problematic at higher flip angles (FA: 43.5°). The potential effect of T2 was modeled and the result was illustrated in FIG. 16A-16B. Without T2 weighting, the signal vs. temperature for the flip angles of 8, 20, 43° would look like FIG. 16A. With T2 weighting (parameters extrapolated from previous work, the echo time and T2 (25 C) was changed to match measured data), the signal model is no longer linear with temperature (FIG. 16B).

The simulation with T2 weighting though based on estimated parameters and not necessarily accurate indicates that T2 weighting could produce the measured results of FIGS. 13A-B. The pattern of non-linear signal vs. temperature results in FIG. 13A was observed over 5 experiments leading to the conclusion that T1-weighted thermometry is not reliable for the UTE echo time of 80 us potentially due to the non-negligible effect of T2 weighting. Decreasing the echo time to decrease T2-weighting is difficult as there are B1 max amplitude issues; in order to decrease the TE, the RF pulse must be shortened. However, the RF pulse has a max B1 amplitude. Shortening the duration of the pulse necessitates decreasing the prescribed flip angle, which leads to increased T2 weighting.

The T1 mapping accuracy of the UTE VIBE variable flip angle method (VFA) was tested by using a $NiCl_2$ phantom. $T_1$ was initially measured using an inversion recovery (IR) 2D turbo spin echo sequence (TSE) to provide a ground truth comparison with VFA.

Figure 17A:
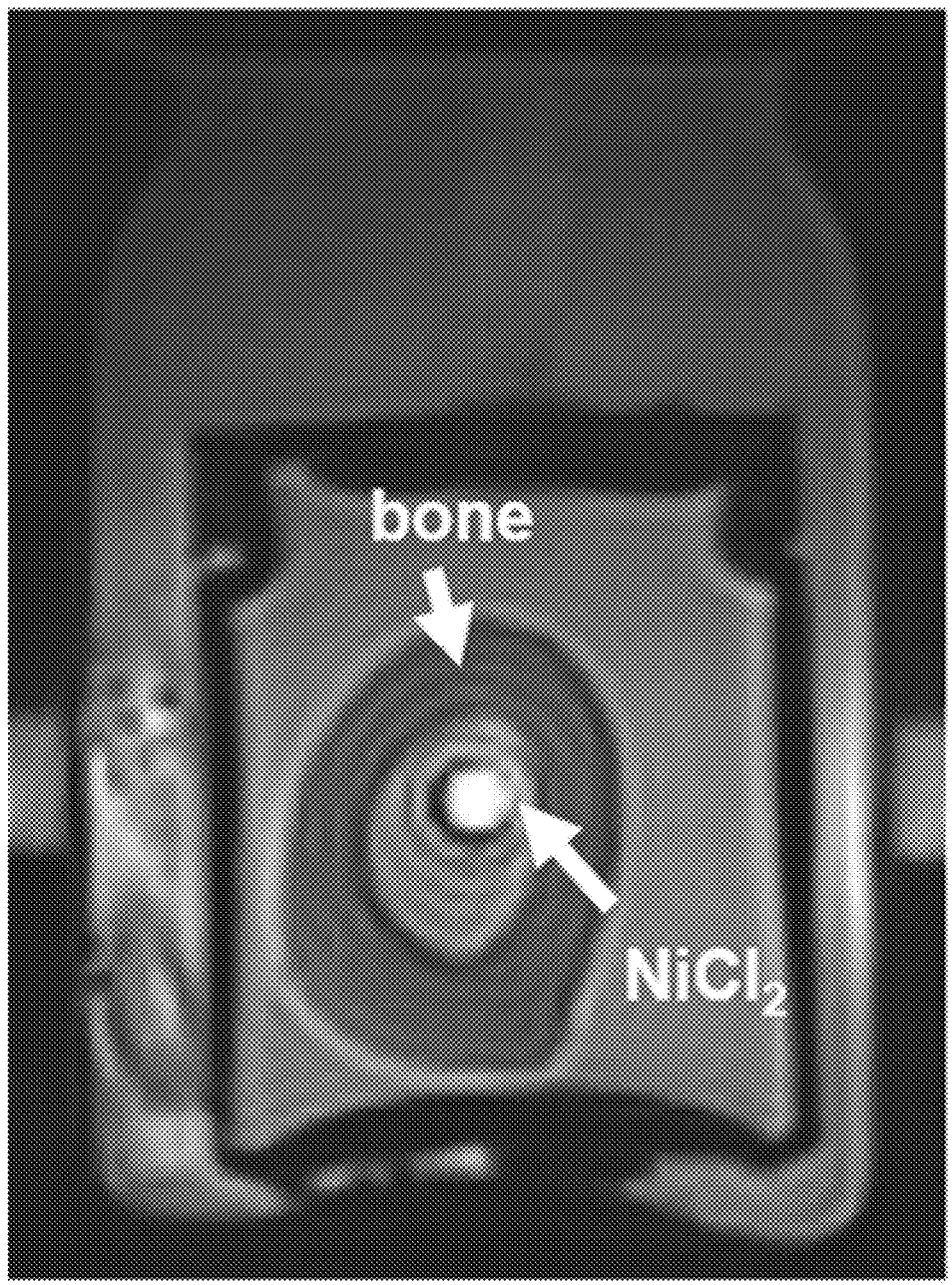
Figure 17B:
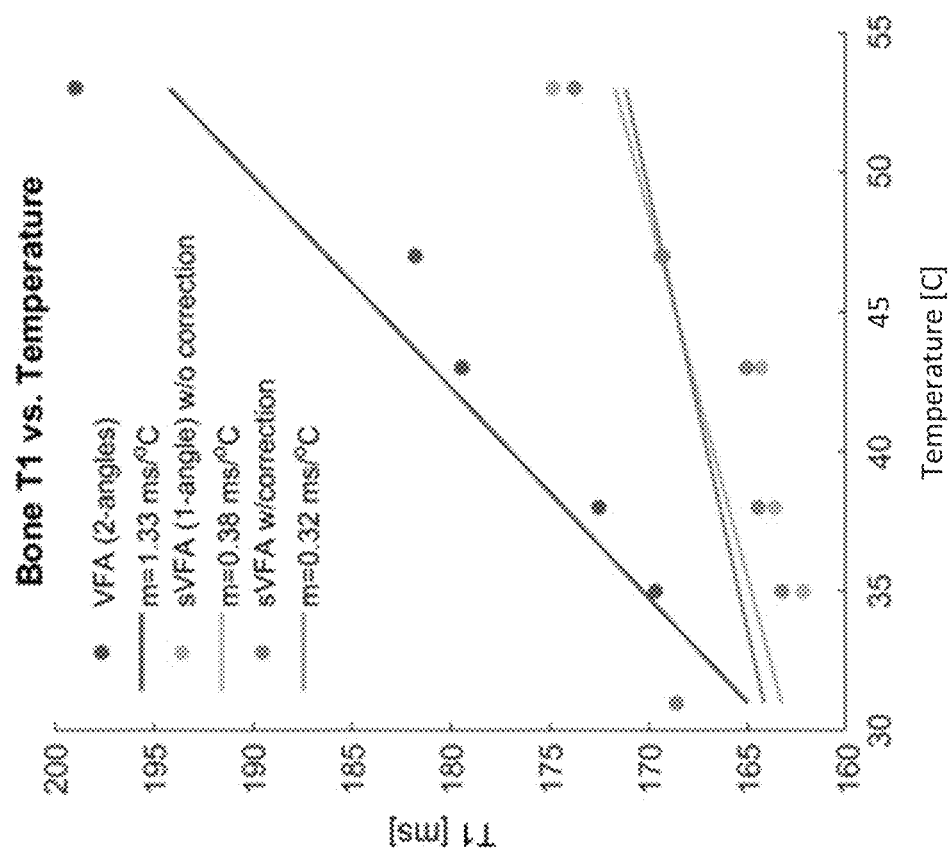
Figure 17C:
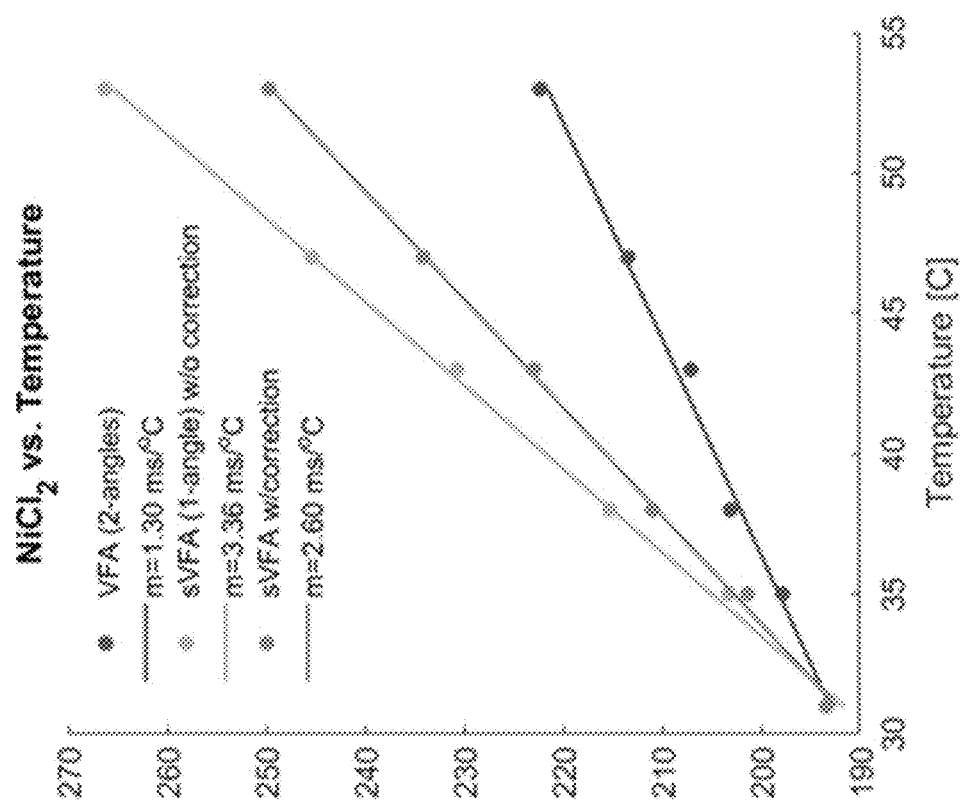
FIG. 17C illustrates the relationship between $NiCl_2$ and temperature. For bone nominal VFA shows T1 has good linearity and slope with temperature.

In the case of $NiCl_2$, the sVFA method without any corrections (using the same reference image for the lower flip angle signal for all temperatures) led to an overestimated T1 vs. Temperature (yellow) compared to the regular VFA measurement (blue) (FIGS. 17A-17C). Svedin et al's model based correction did not work perfectly but did reduce the overestimation. For $NiCl_2$, a more careful application of sVFA would probably bring sVFA measurements closer to the VFA measurements as demonstrated in. However, the sVFA method (with or without model based correction) did not produce a slope similar to the full VFA method for bone. This may be due to neglect of T2 weighting in the method, which is negligible for $NiCl_2$ but not negligible for ultrashort T2 bone as the sVFA method neglects T2 effects.

A cooling experiment was conducted for cow bone cooling in a water bath with an under-sampled UTE VIBE sequence. A linear variable density was chosen (1.1 to 0.7) with ⅝ partial kz, 105 interleaves, (1.625, 1.625, 5 mm) resolution leading to a 1.11 s/kz-encode time (<90 s for two flip angles). A linear T1 trend was observed with reasonable bone T1 values (FIG. 15B). Previous sequences (FIGS. 13A-13B) had a TA of 7.71 s/slice with higher resolution; an acceleration by ~7 times still allows for a measurement of linear T1 changes. Thus, T1-VFA based thermometry is feasible with spiral variable-density acceleration. The slope of T1 vs. temperature for this under-sampled bone image is much higher than previous measurements (averaging 0.98 ms/° C.). The effect of under-sampling on the measured change of T1 with temperature in cow bone remains to be investigated and would provide insight on how under-sampling may affect the calibration of T1 changes with temperature.

To simulate the larger FOV requirement (>280×280×200 $mm^3$), an ex-vivo human skull was imaged. Thermocouples were taped to the skull and it was placed into a bag of 75° C. water and imaged by a 32-channel head coil as it cooled.

The fully sampled and under-sampled sequences were compared. Visually, there were minimal differences between the under sampled and normally sampled scans. Within the same ROI, the baseline T1 was slightly different potentially due to a lower resolution from spiral aliasing resulting in a lower peak at the Ernst angle.

A water bath cooling test was performed in the skull both with and without under-sampling. The results between fully sampled and under-sampled acquisitions had some differences but generally preserved the linear trend between T1 and temperature. Within the same ROI, the baseline T1 was slightly different potentially due to a lower resolution from spiral aliasing resulting in a lower peak at the Ernst angle.

Figure 18B:
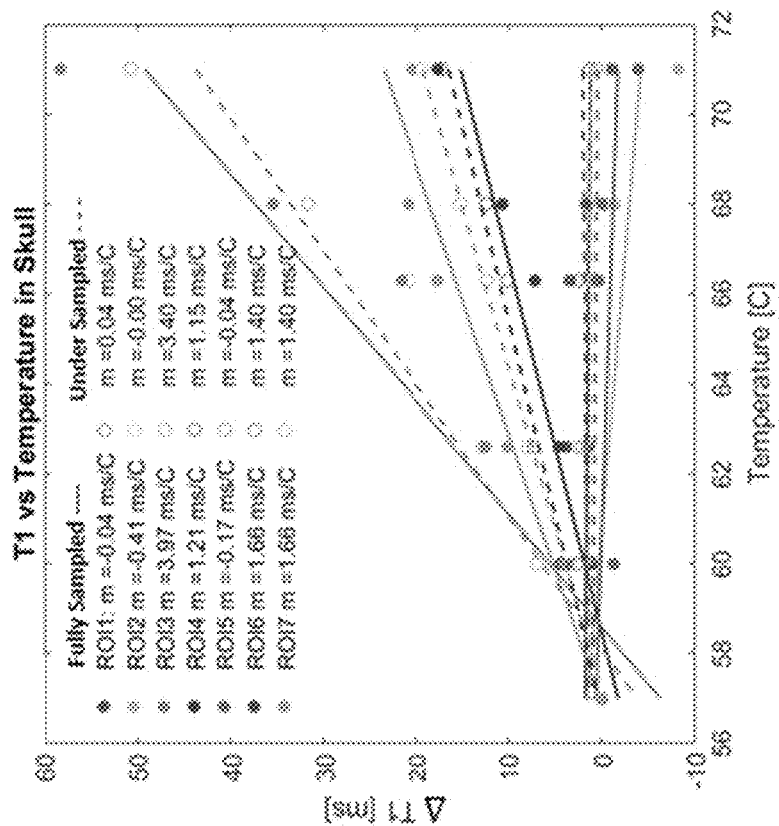
Figure 18A:
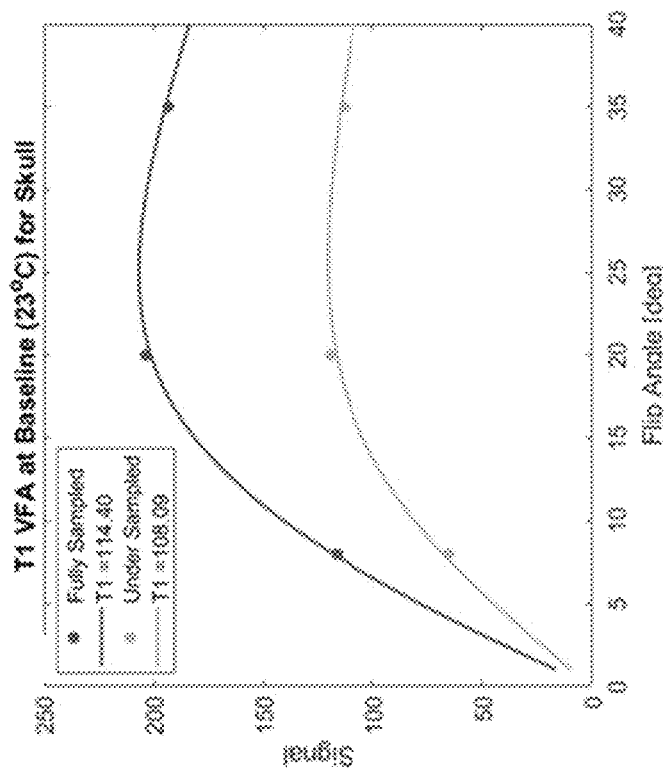

Different ROIs within the skull showed different T1 vs. temperature trends (FIGS. 18A-18B). This could be due to the porosity of the skull with pockets of water in the skull walls. Also, due to the large volume of the skull, the flip angle could vary across the skull and a flip angle correction map should be generated. The baseline T1 value was reasonable and in general either no trend or positive trends in T1 were observed. Repeating this experiment with a higher resolution as the skull is only a few pixels across and potentially with a fresher skull could improve results.

As listed in the non-limiting example of clinical constraints (FIG. 2), MR bone thermometry should be able to detect localized heating caused by FUS. To test the accelerated T1 thermometry method above, a small animal FUS transducer from was used.

Bone was cleaned from fat and marrow, drilled with a hole saw to fit the bone holder, and placed onto an ultrasound transparent film. Initially, water was poured around the bone for ultrasound conduction. However, the movement of water led to blur and other artifacts decreasing image quality. To remove these artifacts, Fomblin was used as a conductive sound medium as well as to mitigate susceptibility distortions in the bone holder. Fomblin, an inert perfluoropolyether flurocarbon, produces no MRI signal but has a similar magnetic susceptibility to tissue. It has been used previously in quantitative and high quality bone imaging by other groups.

Figure 19:
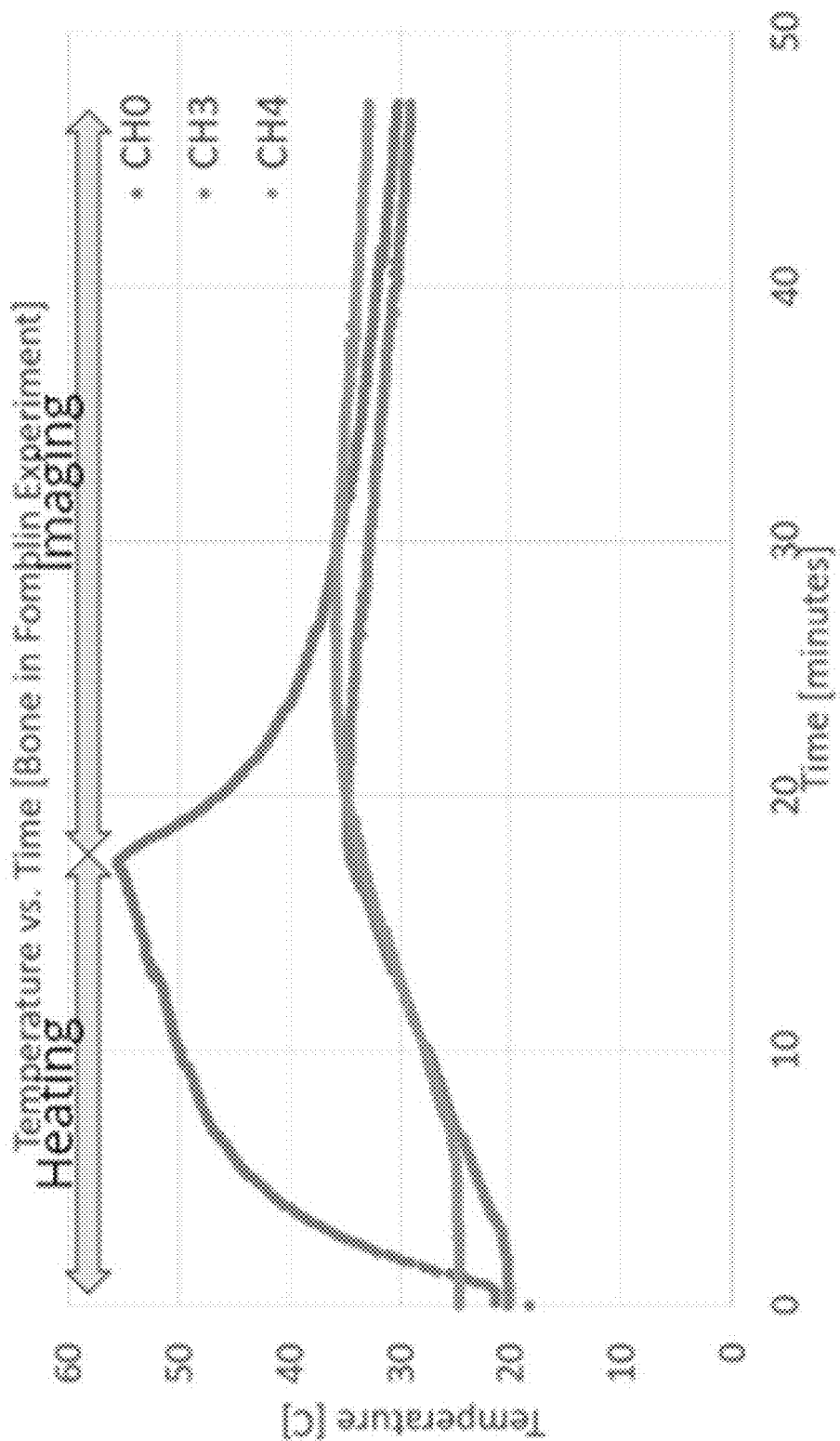
FIG. 19 illustrates the temperature vs. time graph for an embodiment of the present disclosure tested using a sample of bone in fomblin.
Figure 20A:
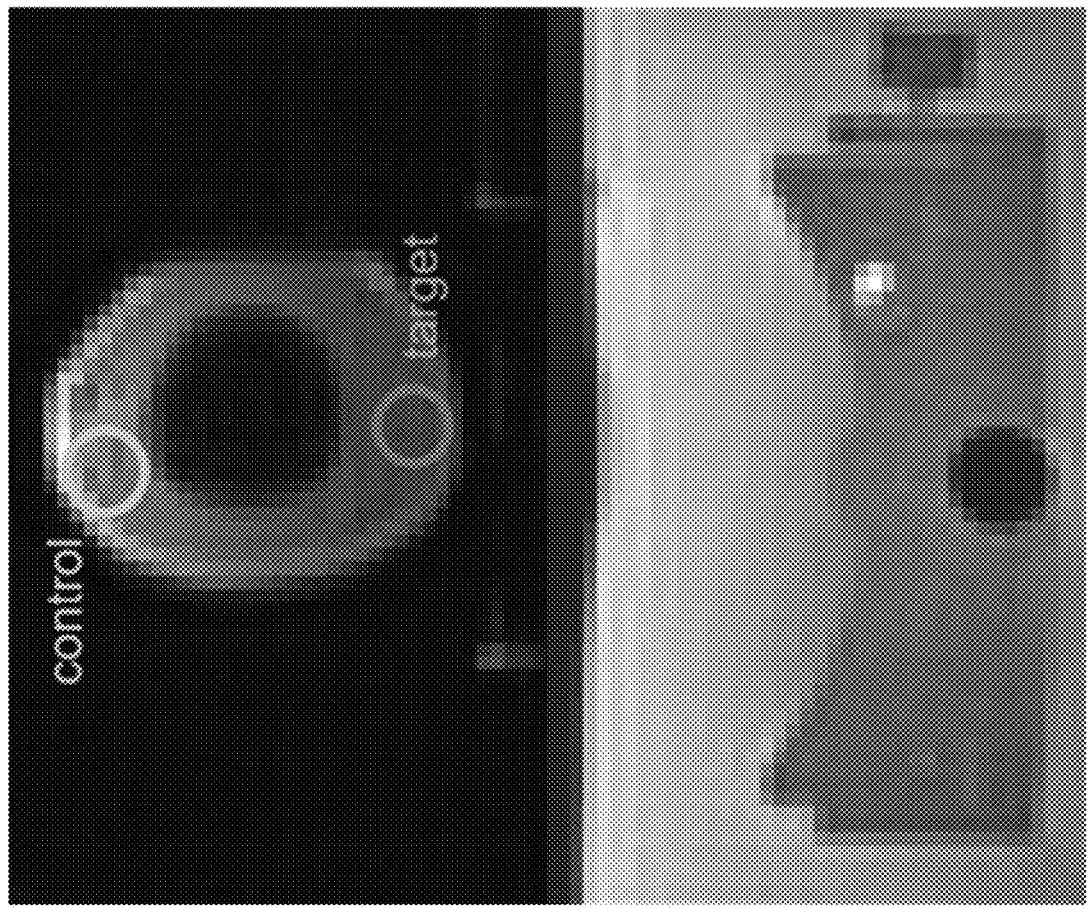
FIGS. 20A-20C illustrate an experimental setup and result where a linear T1 change was detected with temperature in the target.
Figure 20B:
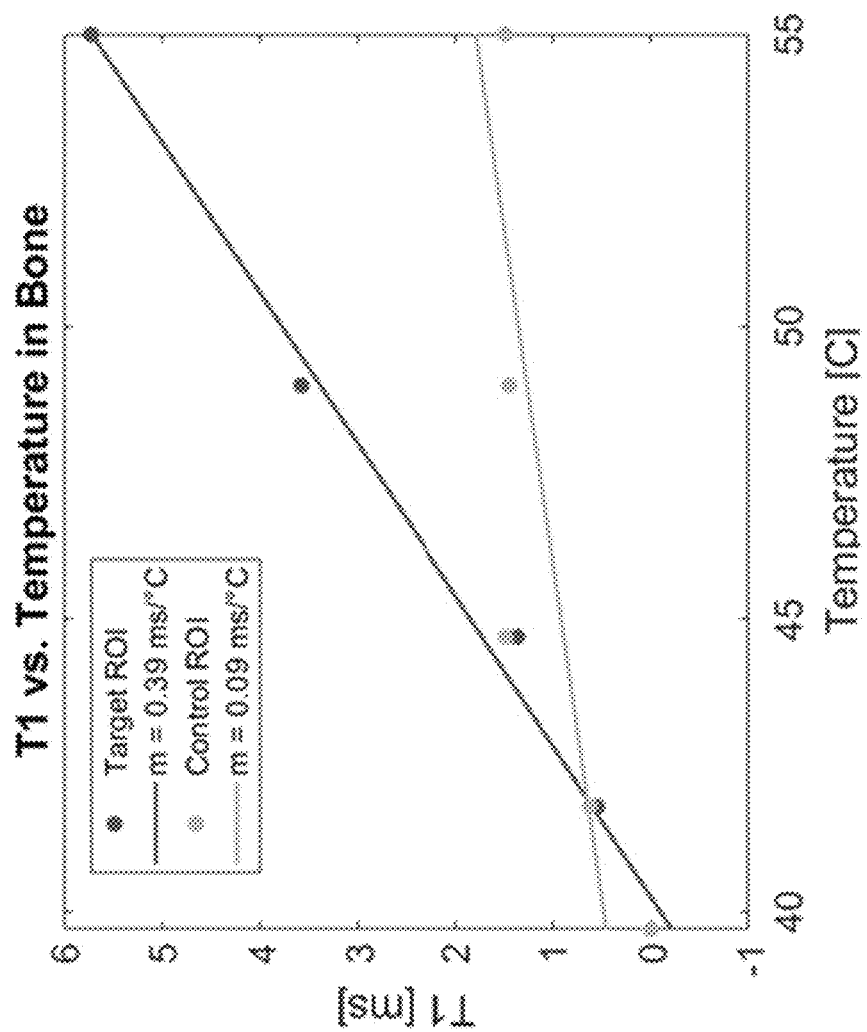
Figure 20C:
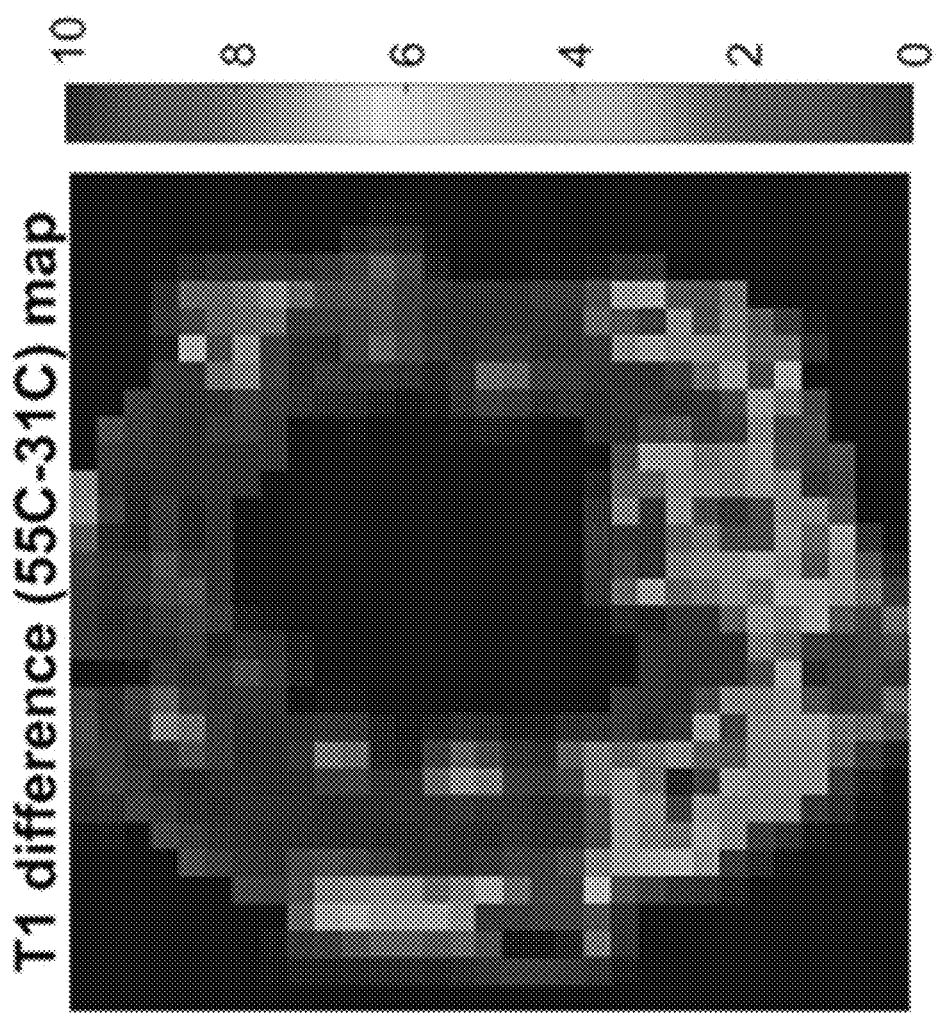

A 4-channel flex coil was used for imaging as the L7 coil (which can be better for this application) could not be used with the FUS setup; the L7 coil requires the use of a spine coil or another L7 coil, and this was not realized until after the experiment. Bone was gradually heated with 8 W for 20 min and imaged; however, images during sonication had strong artifacts. After reaching 53 C, bone was imaged while cooling as shown in FIG. 19.

One relevant clinical goal of T1 mapping thermometry according to some embodiments of the present disclosure is to detect localized heating. One embodiment of the present disclosure that was tested used UTE VIBE T1 thermometry. Bone was placed in Fomblin and heated with focused ultrasound with the results illustrated in FIGS. 20A-20C. A flip angle miscalibration occurred in this experiment but a change in T1 was still detected (0.39 ms/° C.), though less than in previous experiments (0.98 ms/° C.).

A $NiCl_2$ phantom was placed on top of an unfilled (no water) FUS transducer and imaged. Then the water tank was filled and the phantom was imaged again. The T1 decreased significantly (FIGS. 22A-22D). The reference voltage was compared between the (no water tank) FUS setup (255V) and (water) FUS setup (201V); the difference in reference voltage indicated a different B1 calibration readjusted for the water tank which is in turn maladjusted for the bone. Manual RF calibration is thus needed to tune the B1 transmit for the phantom or bone.

With manual flip angle calibration (adjusted $V_{ref}$), the phantom's T1 was correct (the same value as without the FUS transducer). All future experiments which use the FUS transducer may require manual RF calibration if a phantom check fails.

MRgFUS is an important medical technology enabling high-precision non-invasive brain surgery with ultrasound. Examples of medical applications include FDA approved treatment for Parkinson's disease and essential tremor and many other disorders in the research stage such as neuropathic pain, depression, and obsessive-compulsive disorder. One challenge to treatment efficacy is posed by skull heating. Temperature monitoring of the skull would increase treatment safety, enable further development of MRgFUS therapy to non-central brain targets, and potentially speed up treatment by decreasing waiting time between sonications for patients.

Conventional MR thermometry does not work in the skull due to its ultra-short T2, so T1-based thermometry was used. Skull thermometry imaging is generally be fast to capture heating in 90 s, volumetric to detect heating anywhere in the skull, and have a short echo time (<100 us) to enable the imaging of bone. T1 is linear with temperature in cortical cow bone and can thus be calibrated to temperature. However, existing methods have not been demonstrated under clinical constraints and have a long acquisition times (e.g. 8 minutes). Embodiments of the present disclosure employ T1-weighted thermometry using a non-selective ultra-short-echo-time (UTE) 3D spiral sequence. First, T1-weighted thermometry was tested in simpler conditions (cooling of bone in a water bath) and then in more challenging clinically relevant conditions (heating of bone by focused ultrasound).

Analyzing both the T1 values and the T1-weighted signal at different flip angles, it was observed that the trend in T1-weighted signal is not fully linear with temperature. For the same ROIs, T1-mapping results showed a consistent linear trend (0.98+/−0.15 ms/° C.). Thus, T1-mapping with the UTE VIBE was observed to be reliable, linear, and potentially able to be calibrated to indicate skull temperature. However, T1-mapping can be accelerated as part of clinical application. To accelerate T1-mapping, ⅝ partial kz sampling was used and changed the sampling density of the spiral interleaves using linear variable density with full sampling (1) at the center of k-space and 0.7 at the edge of k-space. The under-sampled T1 of bone cooled in a water bath still showed linear results, though the slope was higher the fully-sampled T1 of other bones.

Figure 21:
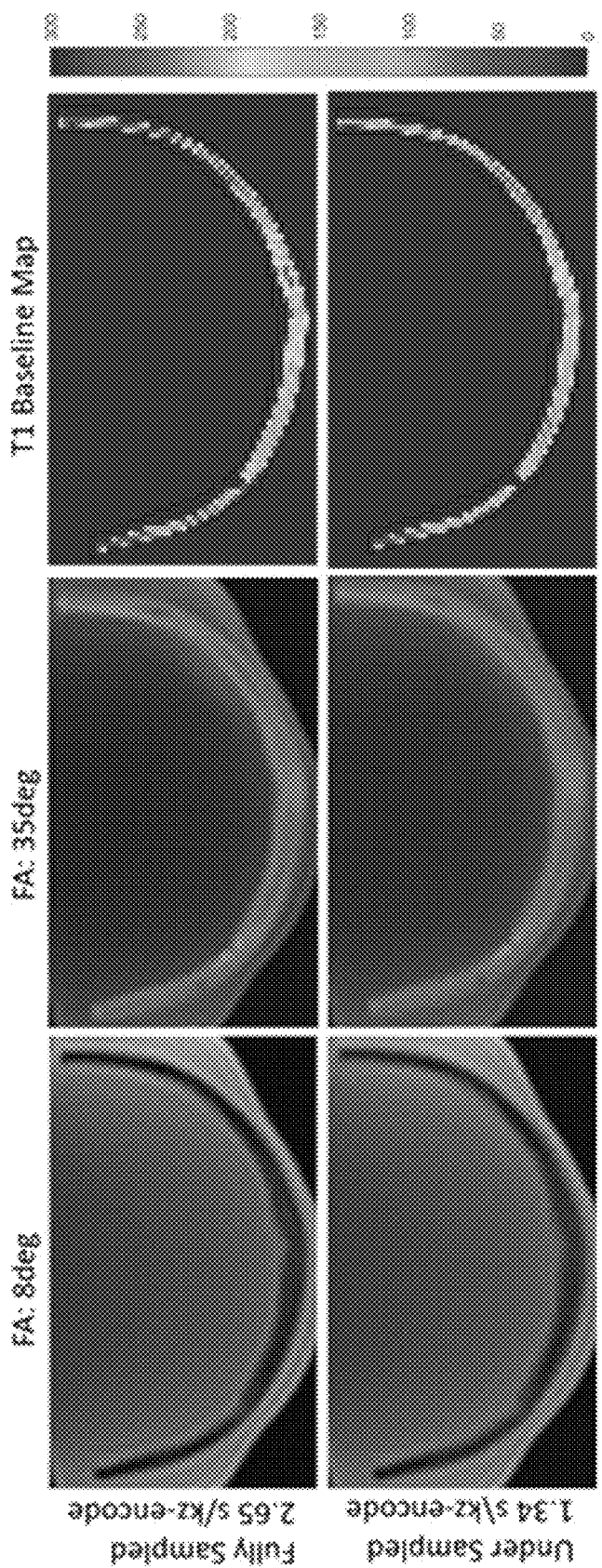
FIG. 21 illustrates fully sampled images (top row) and under-sampled images (bottom row) in which the under-sampled images can be generated approximately twice as fast, even though the image quality is comparable between the images.
Figure 22C:
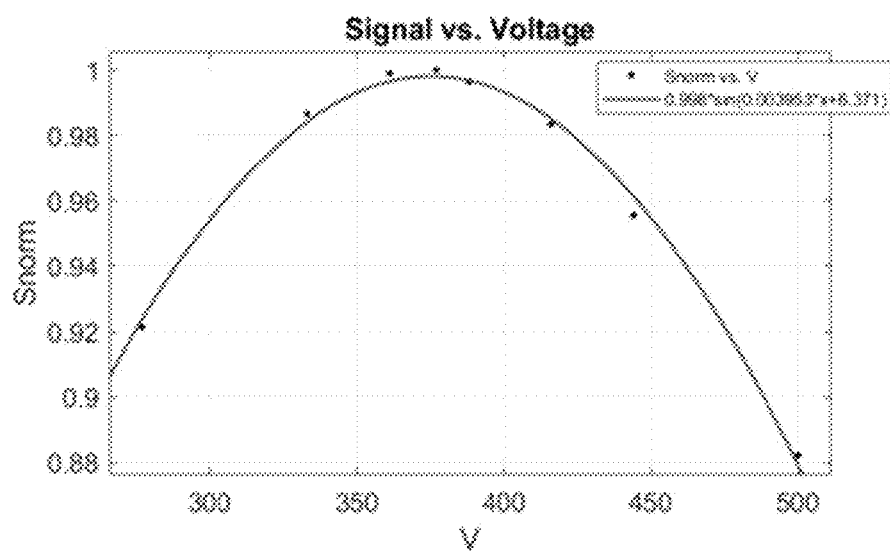
Figure 22D:
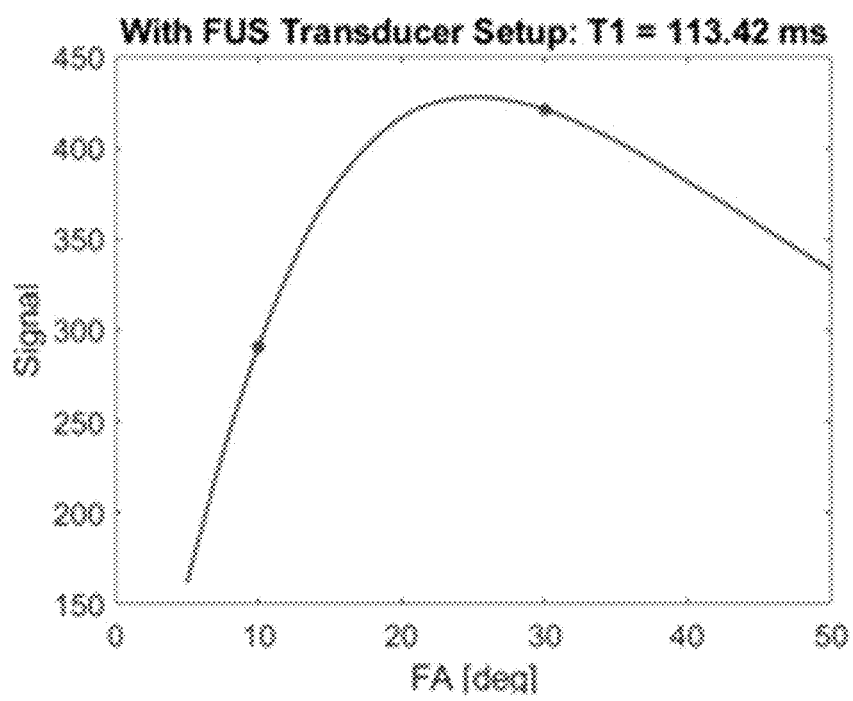

As shown in FIG. 21, there can be minimal differences between under sampled and normally sampled scans, showing that undersampling can be used effectively to accelerate the T1 mapping.

The linear measurements of T1 with temperature in contrast with the variable results of T1 weighted thermometry indicate that UTE VIBE T1 mapping thermometry can have clinical applicability to skull monitoring.

Spiral volumetric T1-mapping thermometry is repeatable and reliable, and that it may be accelerated to potentially meet the clinical constraints (large FOV and short acquisition time). Manual RF calibration combined with a double angle B1 map to check the actual flip angle can also be performed. The use of localized FUS experiments for calibration is also contemplated, for example several trials of localized FUS experiments with L7 coils can be performed (with fat suppression and B1 mapping) on bovine bone. Then, the slope of those trials can serve as a calibration factor to convert T1 onto temperature for another "test" trial to determine method accuracy. Furthermore, the method described herein can be applied to ex-vivo skull experiments, porcine head experiments, and patients.

CONCLUSION

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims, rather than the foregoing description.

What is claimed is:

1. A method for magnetic resonance (MR) based thermometry, comprising:
    acquiring, by a variable flip-angle (VFA) T1 mapping sequence, MR data in an area of interest of a subject corresponding to cortical bone of at least part of the skull that is heated by the application of focused ultrasound (FUS) to a selective portion of the brain of the subject,
    wherein the MR data comprises a plurality of T1 values over time that include a first point in time and a second, later point time, and wherein the acquisition of the MR data comprises applying an accelerated three-dimensional (3D) ultra-short (UTE) spiral acquisition sequence with a nonselective excitation pulse and implementing a spiral readout focused on rapid 3D UTE imaging that comprises changing phase encoding gradient waveform and echo time as a function of the kz-axis; and
    determining, based at least in part on a mathematical relationship established by T1 mapping thermometry produced according to the T1 mapping sequence, a temperature change in the cortical bone that occurs between the first point in time and the second point in time, and wherein the temperature change is caused at least in part by a change in the applied FUS.

2. The method of claim 1, wherein the acceleration of the accelerated 3D UTE spiral acquisition sequence comprises the use of at least one of partial kz acquisition and variable density of spiral interleaves.

3. The method of claim 1, wherein the mathematical relationship is a linear relationship between T1 values and temperature.

4. The method of claim 1, wherein the mathematical relationship is a linear relationship between the change in T1 values over time and a change in temperature over time.

5. The method of claim 1, wherein the change in the FUS corresponds to ceasing of the application of FUS for a period of time determined at least in part on the temperature change in the cortical bone.

6. The method of claim 5, wherein the ceasing for the period of time corresponds to a period of time selected to allow the selective portion of the brain to cool and prevent unintended damage to the brain.

7. The method of claim 6, wherein the FUS resumes after the period of time.

8. The method of claim 1, wherein the change in the FUS corresponds to decreasing the energy applied by the FUS.

9. The method of claim 8, wherein the decreasing of energy applied by the FUS is performed for a period of time selected to allow the skull to cool and prevent unintended damage to the brain.

10. The method of claim 1, wherein the change in the FUS corresponds to decreasing the energy applied by FUS to one or more regions of the skull.

11. The method of claim 1, wherein the acceleration of the accelerated 3D UTE spiral acquisition sequence comprises selecting the sampling density of the spiral interleaves using linear variable density with full sampling at the center of k-space and undersampling at the edge of k-space.

12. The method of claim 1, wherein the selective portion of the brain of the subject corresponds to at least of Parkinson's disease, essential tremor, neuropathic pain, depression, and obsessive-compulsive disorder.

13. The method of claim 2, wherein the partial kz acquisition is selected to reduce scan time by at least about 25%.

14. The method of claim 1, wherein the acquired MR data has a spatial resolution of less than about 5 mm$^3$.

15. The method of claim 1, wherein the area of interest is greater than 280×280×200 mm.

16. The method of claim 1, wherein the steps of acquiring, by the variable flip-angle (VFA) T1 mapping sequence, MR data corresponding to the cortical bone of the subject and determining a temperature change in the cortical bone from the first point in time to the second point in time are performed in less than 90 seconds.

17. A system for magnetic resonance (MR) based thermometry, comprising:
a magnetic resonance imaging (MRI) device configured to acquire, by implementing a variable flip-angle (VFA) T1 mapping sequence, MR data in an area of interest of a subject corresponding to cortical bone of at least part of the skull that is heated by the application of focused ultrasound (FUS) to a selective portion of the brain of the subject,
wherein the MR data comprises a plurality of T1 values over time that include a first point in time and a second, later point time, and wherein the MRI device is further configured to acquire the MR data using an accelerated three-dimensional (3D) ultra-short (UTE) spiral acquisition sequence with a nonselective excitation pulse and implementing a spiral readout focused on rapid 3D UTE imaging that comprises changing phase encoding gradient waveform and echo time as a function of the kz-axis; and
a processor coupled to the MRI device and configured to cause the system to perform functions that include determining, based at least in part on a mathematical relationship established by T1 mapping thermometry produced according to the T1 mapping sequence, a temperature change in the cortical bone that occurs between the first point in time and the second point in time, and wherein the temperature change is caused at least in part by a change in the applied FUS.

18. The system of claim 17, wherein the acceleration of the accelerated 3D UTE spiral acquisition sequence comprises the use of at least one of partial kz acquisition and variable density of spiral interleaves.

19. The system of claim 17, wherein the acceleration of the accelerated 3D UTE spiral acquisition sequence comprises selecting the sampling density of the spiral interleaves using linear variable density with full sampling at the center of k-space and undersampling at the edge of k-space.

20. The system of claim 17, wherein the system further comprises a focused ultrasound (FUS) device configured to apply the focused ultrasound (FUS) to the selective portion of the brain of the subject.

21. The system of claim 17, wherein the mathematical relationship is a linear relationship between T1 values and temperature.

22. The system of claim 17, wherein the mathematical relationship is a linear relationship between the change in T1 values over time and a change in temperature over time.

23. A non-transitory computer-readable medium storing instructions which, when executed by one or more processors of a computing device, cause a system for magnetic resonance (MR) based thermometry to perform functions that include:
acquiring, by a variable flip-angle (VFA) T1 mapping sequence, MR data in an area of interest of a subject corresponding to cortical bone of at least part of the skull that is heated by the application of focused ultrasound (FUS) to a selective portion of the brain of the subject,
wherein the MR data comprises a plurality of T1 values over time that include a first point in time and a second, later point time, and wherein the acquisition of the MR data comprises applying an accelerated three-dimensional (3D) ultra-short (UTE) spiral acquisition sequence with a nonselective excitation pulse and implementing a spiral readout focused on rapid 3D UTE imaging that comprises changing phase encoding gradient waveform and echo time as a function of the kz-axis; and
determining, based at least in part on a mathematical relationship established by T1 mapping thermometry produced according to the T1 mapping sequence, a temperature change in the cortical bone that occurs between the first point in time and the second point in time, and wherein the temperature change is caused at least in part by a change in the applied FUS.

24. The non-transitory computer-readable medium of claim 23, wherein the acceleration of the accelerated 3D UTE spiral acquisition sequence comprises the use of at least one of partial kz acquisition and variable density of spiral interleaves.

25. The non-transitory computer-readable medium of claim 23, wherein the acceleration of the accelerated 3D UTE spiral acquisition sequence comprises selecting the sampling density of the spiral interleaves using linear variable density with full sampling at the center of k-space and undersampling at the edge of k-space.

26. The non-transitory computer-readable medium of claim 23, wherein the mathematical relationship is a linear relationship between T1 values and temperature.

27. The non-transitory computer-readable medium of claim 23, wherein the mathematical relationship is a linear relationship between the change in T1 values over time and a change in temperature over time.

* * * * *